United States Patent
Mahon et al.

(10) Patent No.: US 11,083,387 B2
(45) Date of Patent: Aug. 10, 2021

(54) SYSTEMS AND METHODS FOR DETECTING NERVE FUNCTION

(71) Applicant: SafeOp Surgical, Inc., Hunt Valley, MD (US)

(72) Inventors: Cameron Mahon, Hunt Valley, MD (US); Curt H. Labelle, Hunt Valley, MD (US)

(73) Assignee: SafeOp Surgical, Inc., Hunt Valley, MD (US)

( * ) Notice: Subject to any disclaimer, the term of this patent is extended or adjusted under 35 U.S.C. 154(b) by 773 days.

(21) Appl. No.: 15/034,798

(22) PCT Filed: Nov. 6, 2014

(86) PCT No.: PCT/US2014/064433
§ 371 (c)(1),
(2) Date: May 5, 2016

(87) PCT Pub. No.: WO2015/069949
PCT Pub. Date: May 14, 2015

(65) Prior Publication Data
US 2016/0270679 A1 Sep. 22, 2016

Related U.S. Application Data

(60) Provisional application No. 61/901,345, filed on Nov. 7, 2013, provisional application No. 61/926,876, filed on Jan. 13, 2014.

(51) Int. Cl.
| | | |
|---|---|---|
| *A61B 5/04* | (2006.01) |
| *A61B 5/00* | (2006.01) |
| *A61N 1/04* | (2006.01) |
| *A61N 1/36* | (2006.01) |
| *A61B 5/0478* | (2006.01) |
| *A61B 5/0484* | (2006.01) |

(52) U.S. Cl.
CPC ........ *A61B 5/04001* (2013.01); *A61B 5/0004* (2013.01); *A61B 5/0478* (2013.01);
(Continued)

(58) Field of Classification Search
CPC ........ A61B 5/04001; A61B 2562/0209; A61B 5/4094; A61B 2562/046; A61B 5/0478;
(Continued)

(56) References Cited

U.S. PATENT DOCUMENTS

| | | | |
|---|---|---|---|
| 7,174,206 B2 * | 2/2007 | Frei | A61B 5/4094 |
| | | | 600/300 |
| 8,903,487 B1 * | 12/2014 | Fischell | A61B 5/7282 |
| | | | 607/9 |

(Continued)

FOREIGN PATENT DOCUMENTS

| | | | |
|---|---|---|---|
| JP | 2012236007 A | 12/2012 | |
| WO | WO-01074248 A1 | 10/2001 | |
| WO | WO-2013166157 A1 * | 11/2013 | ......... A61B 5/04001 |

OTHER PUBLICATIONS

Supplemental Partial European Search Report for Application No. EP 14 86 1025, dated Jun. 16, 2017.
(Continued)

*Primary Examiner* — David J. McCrosky
(74) *Attorney, Agent, or Firm* — Mintz Levin Cohn Ferris Glovsky and Popeo, P.C.

(57) ABSTRACT

The present technology relates generally to the field of electrophysiology and specifically to automated devices, components, systems, and related methods for monitoring potential injury to the nervous system using evoked potentials during intraoperative neurophysiologic monitoring.

2 Claims, 25 Drawing Sheets

(52) U.S. Cl.
CPC .......... *A61B 5/0484* (2013.01); *A61B 5/4047* (2013.01); *A61B 5/7225* (2013.01); *A61N 1/0456* (2013.01); *A61N 1/0492* (2013.01); *A61N 1/36014* (2013.01); *A61B 2505/05* (2013.01)

(58) Field of Classification Search
CPC ... A61B 5/0488; A61B 5/6868; A61B 5/4041; A61B 5/4893; A61B 5/6846; A61B 5/053; A61B 5/7282; A61B 6/506; A61B 5/0492; A61B 5/4836; A61B 2505/05; A61B 2017/00039; A61B 5/746; A61N 1/0534; A61N 1/0531; A61N 1/0551; A61N 1/37247; A61M 2205/502; G16H 50/20; G16H 50/30

See application file for complete search history.

(56) References Cited

U.S. PATENT DOCUMENTS

| | | |
|---|---|---|
| 9,744,356 B2 | 8/2017 | Botros et al. |
| 2005/0261559 A1 | 11/2005 | Mumford et al. |
| 2007/0135722 A1 | 6/2007 | Lin |
| 2008/0269835 A1 | 10/2008 | Carlson et al. |
| 2009/0048531 A1 | 2/2009 | McGinnis et al. |
| 2009/0054758 A1 | 2/2009 | Dunseath |
| 2010/0042012 A1 | 2/2010 | Alhussiny |
| 2010/0312124 A1 | 12/2010 | Johnson et al. |
| 2012/0065536 A1 | 3/2012 | Causevic et al. |
| 2012/0095360 A1 | 4/2012 | Runney et al. |
| 2012/0136276 A1 | 5/2012 | Johnson et al. |

OTHER PUBLICATIONS

Zhang et al., "Intraoperative Neurological Monitoring," IEEE Engineering in Medicine and Biology Magazine, vol. 25, No. 4, pp. 39-45, dated Jul. 1, 2016.

Zhao et al., "Adaptive Signal Enhancement of Somatosensory Evoked Potentials Based on Least Mean Squares and Kalman Filter: A comparative Study," Neural Engineering, pp. 738-741, dated Apr. 29, 2009.

International Search Report and Written Opinion for Application No. PCT/US2014/064433, dated Apr. 4, 2015, 10 pages.

Makeig, et al., Mining event-related brain dynamics, Trends in Cognitive Sciences. vol. 8, No. 5, May 2004, pp. 204-210.

\* cited by examiner

Acquiring Evoked Potentials

Each system is stimulated with a series of stimuli:

Stimulus Sequence

Which causes a series of electrophysiological responses that can be detected at specific sites:

Response Sequence

SYSTEMS AND METHODS FOR DETECTING NERVE FUNCTION

CROSS-REFERENCE TO RELATED APPLICATIONS

The present application is a National Stage of International Application No. PCT/US2014/064433, filed Nov. 6, 2014, which claims the benefit of and priority to U.S. Provisional Application Nos. 61/901,345 and 61/926,876, respectively filed on Nov. 7, 2013 and Jan. 13, 2014, and each entitled SYSTEMS AND METHODS FOR DETECTING NERVE FUNCTION, each of which is incorporated herein by reference in its entirety.

FIELD OF THE INVENTION

The present technology relates generally to the field of electrophysiology and specifically to automated devices, systems, and related methods for monitoring potential injury to the nervous system using evoked potentials.

BACKGROUND

In order to facilitate surgical access during many types of surgeries, patients are positioned in ways that may put undue tension or pressure on peripheral nervous structures. This undue tension or pressure can create, what is generally termed, a "positioning effect." Warning signs of positioning effect may include sensations, such as, for example, numbness, tingling, or weakness in a portion of the body. During surgery, a patient is typically placed under general anesthesia and unable to identify the usual warning signs of positioning effect. Consequentially, patients may be left in compromised positions for the duration of a surgical procedure. Continued trauma from positioning effect may result in prolonged or even permanent injury to one or more nerves. An injury caused by positioning effect is known as a "positioning effect injury." The danger of positioning effect injuries has been recognized. Despite surgical teams' careful positioning and padding of structures at risk to positioning effect, positioning effect injuries still occur in significant numbers in many types of surgeries.

Monitoring patients during surgery using conventional attended intraoperative neurophysiologic monitoring (IONM) systems has been shown to allow early identification of impending positioning effect injury; such injury can then be avoided by repositioning the patient to alleviate pressure or tension. Intraoperative monitoring with IONM systems is an accepted and useful clinical service that identifies changes in brain, spinal cord, and peripheral nerve function in order to help prevent the occurrence of long-term or permanent damage to such structures. Conventional IONM systems are not, however, practical for use in many types of surgeries.

SUMMARY

Embodiments described herein generally relate to improved devices, components, systems and methods for IONM, and in some cases are based at least in part upon the recognition of a number of shortcomings associated with IONM. For example, IONM is not automated, not available everywhere, and is expensive. IONM currently requires the constant attendance of a highly trained technologist who connects electrodes on a patient to an IONM instrument designed to evoke, acquire, and process biological signals and display resulting waveforms. It is the job of the technologist to set up the system, connect it to the patient, test the system, and troubleshoot the many technical issues that may prevent accurate and robust recording of the patient's neurophysiological signals. The technologist works under the supervision of a neurologist who monitors and interprets the resultant waveforms to identify conditions such as positioning effect. The waveforms can vary widely in amplitude, frequency, and shape and can evolve throughout the length of a surgery in response to anesthesia and other factors; thus, great skill and expertise is currently needed to meaningfully interpret the waveforms of an IONM system.

The personnel and equipment needed for IONM are limited in availability, require pre-booking, and are costly. Due to the high cost, such monitoring is typically only reimbursed by third party payers for use in surgeries where the risk of severe nerve damage is greatest—surgeries to the brain and spine. As a consequence, monitoring for potential positioning effect injuries and other nerve damage is generally not performed in other types of surgeries where risk of injury to the nerves remains, such as in cardiovascular, urological, and oncological surgeries.

Moreover, due to the current costs and personnel requirements, IONM is not practical for use anywhere outside the operating room even though there are many settings where unresponsive, weak, or immobile patients may incur positioning effect. Thus, in many settings, positioning effect and other nerve injuries remain undetected and the risks of such injuries remain unaddressed.

There is a significant need for improved monitoring systems and techniques to prevent nerve injuries such as positioning effect injuries. In particular, there is a need for an automated detection system that removes the need for the constant attendance of a technologist and eliminates the need for supervision by a neurologist. In the surgical setting, a need exists for devices, systems, and methods that allow a currently available surgical team member, such as an anesthesiologist, to easily monitor for nerve injuries such as positioning effect injuries. A need exists for an inexpensive system for monitoring neurophysiological signals, which is easy to set up, easy to operate, and produces easy-to-interpret results. What is needed is a system that removes many of the technical issues currently encountered during intraoperative neurophysiological monitoring and enables reliable acquisition of desired biological signals. What is also needed is a means of reliably measuring the signals and alerting a clinician not skilled in the art of neurophysiology that the changes in the signal waveforms indicate a pending injury. Additionally, a need exists for a durable, low-cost neurophysiological monitoring device suitable for use in various surgical and non-surgical settings. Various embodiments disclosed herein may fulfill one or more of these needs.

One aspect of the disclosure is directed to a method for detecting the functionality of one or more nerves, for example, by detecting whether said nerves generate acceptable electrical responses upon stimulation. In some embodiments, the method includes: outputting a plurality of time-locked electrical stimuli to a stimulating electrode positioned on a body; recording a plurality of resultant electrical waveforms received from a recording electrode positioned on the body, the resultant electrical waveforms generated by the body's nervous system in response to the time-locked electrical stimuli; developing an initial baseline waveform from an average of the plurality of resultant electrical waveforms; outputting an additional electrical stimulus to the stimulating electrode; recording an additional resultant electrical waveform from the recording electrode; and determining if the additional resultant electrical waveform is acceptable by comparing the additional resultant electrical waveform to the initial baseline. In some embodiments, if the additional resultant electrical waveform is acceptable, the method further includes developing an updated baseline waveform, wherein the updated baseline waveform is a weighted average of the initial baseline waveform and the additional resultant electrical waveform. In some embodiments, the method further includes sending a data output to a user interface, the data output comprising an indication of whether the additional resultant electrical waveform is acceptable.

Another aspect of the disclosure is directed to a non-transitory computer readable medium, which stores instructions. In some embodiments, the instructions, when implemented, cause a processor to perform a method, such as, for example, an embodiment of the method described above.

Another aspect of the disclosure is directed to an automated device for detecting evoked potentials in a patient. In some embodiments, the device includes a non-transitory computer readable medium, such as the computer readable medium described above or elsewhere in this disclosure. In some embodiments, the device further includes: a processor configured to execute instructions stored on the non-transitory computer readable medium; a signal output configured to couple to a stimulating electrode; a signal input configured to couple to a recording electrode; and a data output configured to send processed data to a user interface.

An additional aspect of the disclosure is directed to a system for detecting positioning effect in a body. The system of some embodiments includes: a signal output operable to couple directly or indirectly to a stimulating electrode to deliver an electrical stimulus to a peripheral nerve in the body; a signal input operable to couple directly or indirectly to a recording electrode to record a resultant electrical waveform generated by the body's nervous system in response to the electrical stimulus; a signal generation circuit and/or processor coupled to the signal output and the signal input and configured to generate the electrical stimulus and process the resultant electrical waveform; and a detection processor configured to detect a positioning effect by calculating a moving baseline and comparing the processed resultant electrical waveform to the moving baseline. In various embodiments, processing the resultant electrical waveform includes filtering and/or amplifying the resultant electrical waveform.

In some embodiments of the system, the signal generation processor and the detection processor form part of the same processor. In other embodiments, the signal generation circuit and/or processor is separably electrically coupled to the detection processor. For example, in some embodiments, the signal generation circuit and/or processor can be connected to the detection processor via a cable or other connection means. In other embodiments, the system also includes a first wireless antenna coupled to the signal generation processor and a second wireless antenna coupled to the detection processor; in such embodiments, the signal generation processor is in wireless communication with the detection processor. In some such embodiments, the first and second wireless antennas are each selected from the group consisting of: a wireless transmitter, a wireless receiver, and a wireless transmitter/receiver.

An additional aspect of the disclosure is directed to another system for detecting positioning effect in a body. The system of some embodiments includes: a signal output operable to couple directly or indirectly to a stimulating electrode to deliver an electrical stimulus to a peripheral nerve in the body; a signal input operable to couple directly or indirectly to a plurality of recording electrodes to record resultant electrical waveforms generated by the body's nervous system in response to the electrical stimulus; a signal generation circuit and/or processor coupled to the signal output and the signal input and configured to generate the electrical stimulus and process the resultant electrical waveforms; a detection processor configured to detect a positioning effect from the processed resultant electrical waveforms; and the stimulating electrode. The system further includes a plurality of recording electrodes, reference electrodes, and ground electrodes positioned at a plurality of peripheral recording sites, wherein each peripheral recording site has one ground electrode, one reference electrode, and one recording electrode, and wherein the recording electrode and the reference electrode are positioned between the ground electrode and the signal input. In some such embodiments, the reference electrode, the recording electrode, and the ground electrode are all disposed on a single electrode unit. In other embodiments, two electrodes: the recording electrode and the ground electrode are disposed on a single electrode unit.

In some embodiments disclosed herein, a system for detecting positioning effect in a body includes: a signal output operable to couple directly or indirectly to a stimulating electrode to deliver an electrical stimulus to a peripheral nerve in the body; a signal input operable to couple directly or indirectly to a recording electrode to record a resultant electrical waveform generated by the body's nervous system in response to the electrical stimulus; a signal generation circuit and/or processor coupled to the signal output and the signal input and configured to generate the electrical stimulus and process the resultant electrical waveform; a detection processor configured to detect a positioning effect from the processed resultant electrical waveform; the stimulating electrode; and the recording electrode. In some such embodiments, at least one of the stimulating electrode and recording electrode comprise a wet gel electrode.

In other embodiments, the system for detecting positioning effect in a body may include: a signal output operable to couple indirectly to a stimulating electrode to deliver an electrical stimulus to a peripheral nerve in the body; a signal input operable to couple indirectly to a recording electrode to record a resultant electrical waveform generated by the body's nervous system in response to the electrical stimulus; a signal generation circuit and/or processor coupled to the signal output and the signal input and configured to generate the electrical stimulus and process the resultant electrical waveform; a detection processor configured to detect a positioning effect from the processed resultant electrical waveform; a first triaxially shielded cable coupled to, and connecting, the signal output and the stimulating electrode; and a second triaxially shielded cable coupled to, and connecting, the signal input and the recording electrode.

An additional aspect of the disclosure is directed to a method for detecting positioning effect in a body. In some embodiments, the method includes: generating an electrical stimulus; delivering the electrical stimulus to a peripheral nerve in the body; recording a resultant electrical waveform generated by the body's nervous system in response to the electrical stimulus; processing the resultant electrical waveform; and detecting a positioning effect at least in part by calculating a moving baseline and comparing the processed resultant electrical waveform to the moving baseline.

In some embodiments of the method, the resultant electrical waveform is recorded at a plurality of peripheral recording sites using a plurality of single electrode units, each single electrode unit having a ground electrode, a reference electrode, and a recording electrode. In some embodiments of the method, delivering the electrical stimulus involves delivering the electrical stimulus from an output, through a triaxially shielded cable, to a stimulating electrode. In some embodiments of the method, recording the resultant electrical waveform involves receiving the resultant electrical waveform at a recording electrode and sending the resultant electrical waveform through a triaxially shielded cable to an input. Additionally or alternatively, in some embodiments, delivering the electrical stimulus involves delivering the electrical stimulus via a wet gel electrode. Similarly, in some embodiments, recording the resultant electrical waveform involves receiving the resultant electrical waveform via a wet gel electrode.

In an additional aspect of the disclosure a system for detecting positioning effect in a body includes: a signal output operable to couple directly or indirectly to a stimulating electrode to deliver an electrical stimulus to a peripheral nerve in the body; a signal input operable to couple directly or indirectly to a recording electrode to record a resultant electrical waveform generated by the body's nervous system in response to the electrical stimulus; a radio frequency receiver; a signal generation circuit and/or processor coupled to the signal output and the signal input and configured to generate the electrical stimulus and process the resultant electrical waveform; and a detection processor configured to detect a positioning effect from the processed resultant electrical waveform. In some such embodiments, the signal generation processor and/or the detection processor is configured to detect a radiofrequency signal received from the radiofrequency receiver and cease signal acquisition upon detection of the radiofrequency signal.

A further aspect of the disclosure is directed to a method of automating the startup and testing protocols of an evoked potential detection device. In some embodiments, the method includes: receiving an input to start testing of an evoked potential detection device or to start recording evoked potentials; automatically detecting impedance of an acquisition electrode; determining if the impedance level is acceptable; transmitting an output indicating whether the impedance level is acceptable; and permitting signal acquisition only from one or more acquisition electrodes having acceptable impedance levels. In some embodiments, the method also includes: initiating a stimulation protocol at a default stimulation level; increasing the stimulation level; and monitoring the size of a resultant electrical waveform. In some such embodiments, if the resultant electrical waveform increases with an increasing stimulation level, the stimulation level is repeatedly increased until the resultant electrical waveform no longer increases; if the resultant electrical waveform does not increase with an increasing stimulation level, the default stimulation level is maintained.

Another aspect of the disclosure is directed to a non-transitory computer readable medium storing instructions, which when implemented, cause a processor to perform an automated method of testing and/or detecting, such as, for example, the method described above or elsewhere herein.

Another aspect of the disclosure is directed to an automated device for detecting evoked potentials in a patient. In some embodiments, such a device includes a non-transitory computer readable medium, such as the computer readable medium described above or elsewhere herein, a processor configured to execute instructions stored on the non-transitory computer readable medium, a signal output configured to couple to a stimulating electrode, and a signal input configured to couple to a recording electrode.

DETAILED DESCRIPTION

Figure 1:
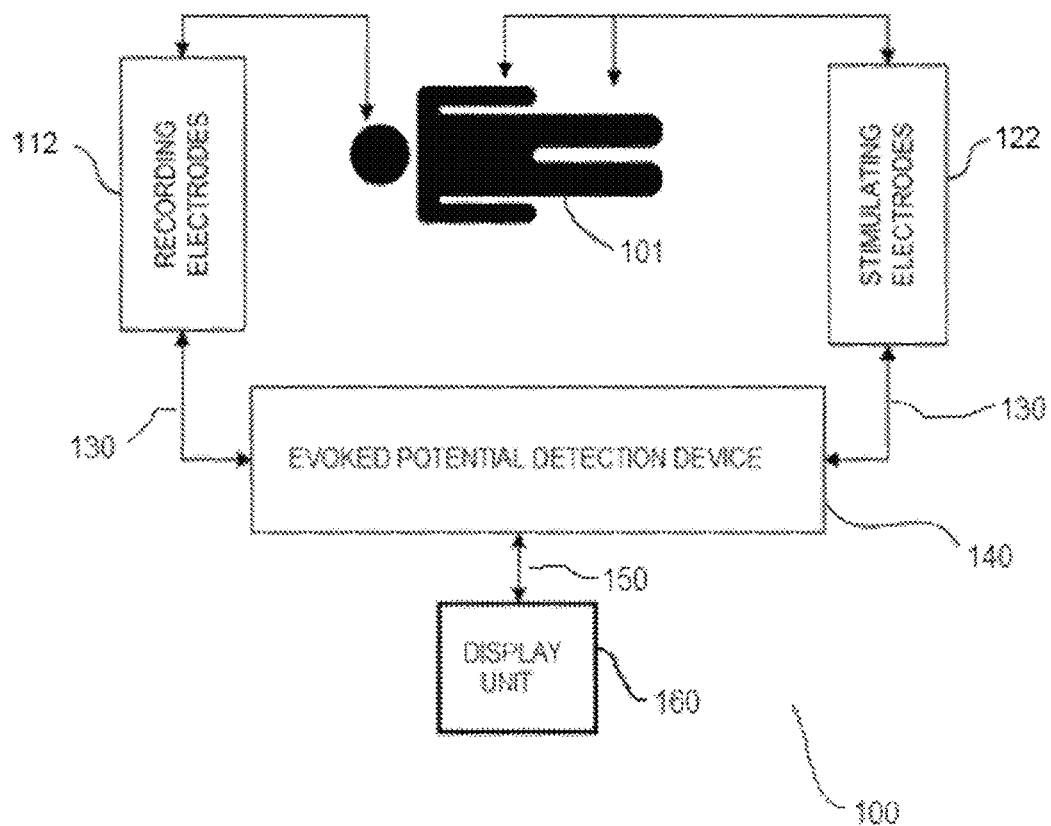
FIG. 1 depicts a functional block diagram of one embodiment of a system for monitoring nerve function.

In the following detailed description, reference is made to the accompanying drawings and the accompanying appendix, which form part of the present disclosure. The embodiments described in the drawings and description are intended to be exemplary and not limiting. As used herein, the term "exemplary" means "serving as an example or illustration" and should not necessarily be construed as preferred or advantageous over other embodiments. Other embodiments may be utilized and modifications may be made without departing from the spirit or the scope of the subject matter presented herein. Aspects of the disclosure, as described and illustrated herein, can be arranged, combined, and designed in a variety of different configurations, all of which are explicitly contemplated and form part of this disclosure.

Unless otherwise defined, each technical or scientific term used herein has the same meaning as commonly understood by one of ordinary skill in the art to which this disclosure belongs. In accordance with the claims that follow and the disclosure provided herein, the following terms are defined with the following meanings, unless explicitly stated otherwise.

The term "about" or "approximately," when used before a numerical designation or range (e.g., pressure or dimensions), indicates approximations which may vary by (+) or (−) 5%, 1% or 0.1%.

As used in the specification and claims, the singular form "a", "an" and "the" include both singular and plural references unless the context clearly dictates otherwise. For example, the term "an electrode" may include, and is contemplated to include, a plurality of electrodes. At times, the claims and disclosure may include terms such as "a plurality," "one or more," or "at least one;" however, the absence of such terms is not intended to mean, and should not be interpreted to mean, that a plurality is not conceived.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a device or method consisting essentially of the elements as defined herein would not exclude other materials or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

"Evoked potential" shall mean any electrical potential recorded from the nervous system, which results from the application of a stimulus to a portion of the body. Evoked potentials include, for example, somatosensory evoked potentials (SEPs), visual evoked potentials (VEPs), motor evoked potentials (MEPs), and brain stem auditory evoked potentials (BAEPs).

"Somatosensory evoked potentials," also known as "SSEPs" or "SEPs," and referred to herein as "SEPs," shall refer to the electrical signals generated by the nervous system in response to an electrical stimulus of a peripheral nerve.

As used herein, a "support structure" shall refer to a bed, a chair, a wheelchair, a stretcher, a gurney, an operating room table, a pre-op table, a post-op table, and/or any other device configured to provide support to a patient, particularly a weak, immobile, or unconscious patient.

Various devices, systems, and methods disclosed herein allow for non-expert monitoring of a patient's nervous system, where expert is defined as an expert in neurology or neurophysiology or a trained neurophysiology technologist. While such an expert also can practice and utilize the technology, he/she is not required due to the nature of the technology described herein. Embodiments provided herein are largely directed to the detection of potential or impending injuries to peripheral and/or cranial nerves. One of ordinary skill in the art will appreciate that while many embodiments disclosed herein describe detection of positioning effect for the sake of simplicity of the description, all such embodiments may also be used to detect potential or impending injuries to the optic nerve or other potential nerve damage to peripheral and/or cranial nerves. Moreover, one of ordinary skill in the art will appreciate that while many embodiments disclosed herein are directed to the detection of SEPs for the sake of simplicity of the description, various embodiments may also be used to detect MEPs, VEPs, and other evoked potentials.

Introduction

As described above, impending positioning effect injuries can be detected using intraoperative neurophysiologic monitoring (IONM) systems; in particular, such injuries can be detected by using IONM systems to monitor SEPs generated in response to electrical stimulation of a peripheral nerve. Acute changes in SEPs, such as, for example, decreases in amplitude or size (i.e., area) or increases in latency of the SEP waveform, can be indicative of a pending nerve injury. As one non-limiting example, a 30-50% decline in amplitude or a 3 millisecond or 10% increase in latency, relative to a baseline, may indicate an impending nerve injury.

Compared to other biological signals, SEPs are typically very small having amplitudes of less than a microvolt to several microvolts. In comparison, the amplitude of many other recorded biological signals, such as EEG, EMG, and ECG, tend to be much larger. A typical EEG is usually 10 or more microvolts, EMG is one or more millivolts and an ECG signal can be hundreds of millivolts. The relative size of these other biological signals has meant that acquiring and monitoring such signals has been much easier to incorporate into standard surgical practice. In contrast, despite the clinical utility of SEPs, their small size has limited their use to specialized surgeries that justify having a technologist and/or neurologist present.

Recording SEPs reliably with existing technology is difficult and requires a person with expertise in the practice to ensure that electrical interference is minimized. The smaller the biological signal, the more important it is to limit the electrical noise contamination of the recording. Noise is produced when other electrical signals are picked up by, and coupled into, the recording circuits of the monitoring system. This contaminating noise can occur at any point along the acquisition circuit, including within the patient, at the site of the electrodes, within the cables carrying the unamplified signals, and at the location of signal amplifiers.

To record SEP microvolt signals in an electrically noisy environment such as the operating room, surgical technologists employ a myriad of techniques to increase the signal-to-noise ratio of the SEP.

For example, the surgical technologists take great care in setting up the electrode sites. To record the SEPs, medical devices use a differential amplifier, which amplifies the voltage difference between two electrodes. These two electrodes, which are commonly referred to as the "active" and "reference" electrodes, are typically placed within a few centimeters of each other on the patient by the surgical technologist. The capability of a differential amplifier to reject unwanted but common input signals, relative to the desired differential signal is referred to as the "common-mode rejection ratio" (CMRR). An ideal differential amplification system would have an infinite CMRR but current amplification technology limits the CMRR. Keeping the CMRR at high levels is essential to minimizing electrical noise interference in the acquisition system. Currently, to maintain a high CMRR for intraoperative neuromonitoring, the surgical technologist must carefully prepare the skin underneath the active and reference electrodes to achieve similar low impedances. To reduce noise, needle electrodes are commonly used.

Figures 25A, 25B:
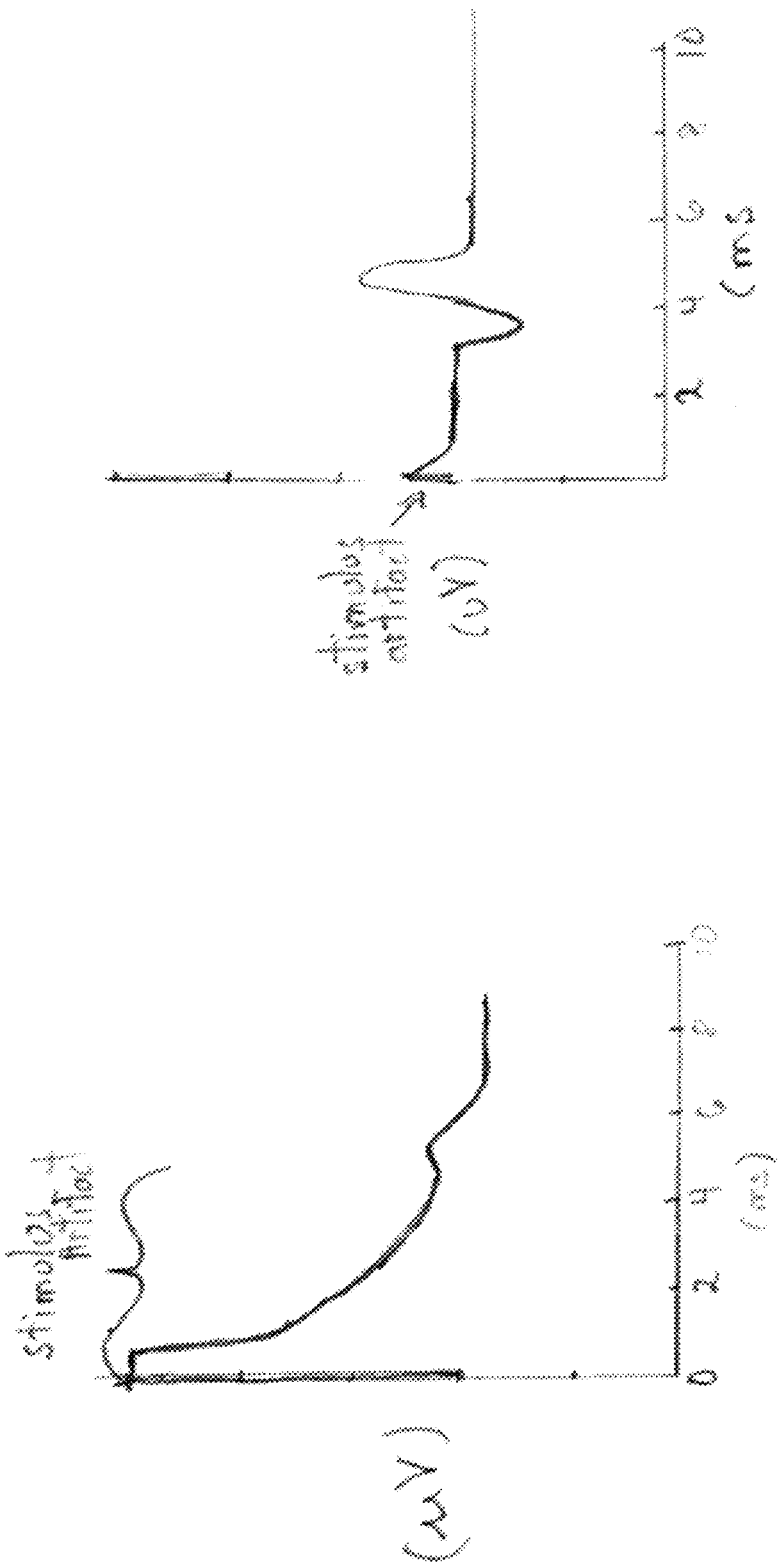

The patient's body can act as an antenna and conduct electrical noise. Each electrode attached to the patient will carry this noise to the amplifiers of the SEP detection device. To overcome this, the surgical technologist typically includes a single grounding electrode within the system. The grounding electrode provides a path for the electrical noise in order to reduce the amount that enters the amplification system. The grounding electrode also serves as a means to shunt the SEP stimulation voltage away from the amplification system. The stimulating voltage can be up to 300 volts, and without the grounding electrode, the stimulating voltage would saturate the SEP amplifiers that are optimized to manage microvolt signals. The saturation of the amplifiers by the stimulus is referred to as stimulus artifact. If the amplifiers are unable to recover from the large pulse from the stimulation in a few milliseconds, they will not be able to amplify the SEP waveform (see FIG. 25A where the first stimulus artifact obscures the beginning of the waveform and changes the amplitude, whereas in FIG. 25B, the amplifier has recovered from the stimulus artifact allowing for accurate measurement of the onset and amplitude of the response). To minimize the amount of stimulus artifact, the technologist will often do one or more of the following: reorient the stimulator to change the direction of the electrical field, move the stimulation cable away from the recording electrode cable, decrease the duration of the stimulating pulse, and remove and replace the stimulator after preparing the skin to reduce the impedance.

Additionally, to reduce noise in the system, the surgical technologist often twists the cables of the recording and active electrodes to reduce the amount of uncommon noise that is coupled into the system. The technologist also continually monitors the waveforms to determine if excessive noise is present and will make adjustments to the setup during surgery, as needed. For example, the technologist may repeatedly move the system's unshielded cables during surgery when they get close to any electrical noise generators such as power cables, patient warming devices, and other electronic surgical instrumentation.

Moreover, SEPs are typically not visible in the raw data when a single stimulus is applied. To extract the SEP waveforms from the background noise, the surgical technologist generally uses an IONM system that applies successive time-locked stimuli. Multiple stimulus time locked recording epochs are averaged together. For example, various IONM systems stimulate peripheral nerves at a frequency of 2 to 5 Hz, and averaged waveforms are acquired for analysis when 300 to 500 stimuli have been delivered. Because other noises are random and not time locked to the stimulus, such noise will largely cancel out.

With some surgical instrumentation, such as electrosurgical units (ESUs), also known as RF knives or Bovies, the noise is known to be so large that the system is unable to remove this interference using the normal means of averaging time-locked waveforms. Some technologists will simply assume a signal is contaminated with noise from the ESU and reject or disregard the signal if it gets within a particular threshold value, for example, 95%, of the maximum positive or negative value of an analog-to-digital converter (ADC) in the system. Such an approach is lacking in sensitivity and specificity. Low levels of ESU interference may avoid rejection and still be present in the signal, and lowering the filter level to capture these low levels of ESU interference may cause rejection of normal SEP signals too. Other technologists simply turn off the acquisition of signals manually when an ESU is in use. This can be a tedious process since ESUs are used frequently during surgery to cut and cauterize tissue.

Surgical technologists remain attuned to the procedures occurring in the surgical room and often mentally factor such procedures into the analysis of the waveforms. For example, a technologist may mentally disregard changes to waveforms that are observed within a time frame following the application of an anesthetic agent or declining waveforms that are observed concurrently with declining blood pressure or heart rate. A technologist may also mentally disregard system-wide waveform changes detected at all recording sites.

Various embodiments described herein are directed to devices, components, systems, and/or methods that simplify and/or automate one or more of the above functions of a surgical technologist such that SEP and/or other evoked potential monitoring may be possible without a surgical technologist present. Some of the various embodiments make evoked potential monitoring significantly easier and cheaper such that it can become a ubiquitous surgical practice.

System Overview

FIG. 1 depicts a block diagram of a system for automatically detecting evoked potentials in accordance with one embodiment of the present disclosure. In the depicted embodiment, the system 100, which may be coupled to a patient 101, includes, but is not limited to, one or more recording electrodes 112, one or more stimulating electrodes 122, an evoked potential detection device (EPDD) 140, and a display unit 160.

In some embodiments of the system 100, the stimulating electrodes 122 are configured for placement on or near the arms or legs of a patient 101 over peripheral nervous structures such as, for example, the ulnar nerves, median nerves, peroneal nerves, and/or posterior tibial nerves. In some embodiments, the stimulating electrodes 122 are intended for placement on a patient's skin on the wrists and ankles so that the electrodes are located over or near the ulnar nerves and posterior tibial nerves. Such a configuration allows for full patient monitoring of peripheral nerves (i.e., monitoring of nerves in all limbs). In other embodiments, the system 100 may be used for upper limb monitoring only; in such embodiments, the stimulating electrodes 122 may be intended for placement on the skin of a patient's wrists, for example, over or near the ulnar nerves only.

The recording electrodes 112 of some embodiments are configured for placement over the trunk, spine, neck, and/or head. In some embodiments, the recording electrodes 112 are intended to be placed on the skin on or over one or more of the following locations: cervical vertebra 5 (C5) just below the hairline, the forehead, the left and right Erb's points near the clavicle, and the left and right Popliteal Fossa just above the knee.

In various embodiments, the EPDD 140 is electronically coupled to the recording electrodes 112 and stimulating electrodes 122 via a plurality of cables 130. The EPDD 140 of various embodiments forms part of, is coupled to, and/or includes a computer, such as, for example, the computer described in further detail below with reference to FIG. 2. In various embodiments, the EPDD 140 is also electrically, electronically, and/or mechanically coupled to the display unit 160 via a link 150. In some embodiments, the link 150 is internal wiring or external cable. In some embodiments, the link 150 is a wireless communication link. For example, in some embodiments, the EPDD 140 is wirelessly coupled to the display unit 160 via Bluetooth® or other radiofrequency signal or via near field communications or a cellular signal.

According to an exemplary embodiment, the EPDD 140 applies electrical stimulation to peripheral nerves of a patient by sending electrical signals to the stimulating electrodes 122 located on some or all of a patient's limbs. Repeated stimulation elicits a response of the patient's nervous system in the form of SEPs, which travel up the peripheral nerves, through the dorsal column of the spinal cord, and to the brain. With the right equipment, SEPs can be detected and changes in the evoked potential monitored to assess changes in nerve function. In an exemplary embodiment, the EPDD 140 uses the recording electrodes 112 to detect generated SEPs. The EPDD 140 of some embodiments includes software, which when executed, causes the EPDD 140 to detect changes in the SEPs, such as, for example, changes in latency, changes in amplitude, or changes in morphology. Based on the observed changes, the EPDD 140 of some embodiments may identify potential positioning effect injuries caused by a physical position of the patient's body. Changes such as reductions in amplitude or overall waveform size (i.e., area) or increases in latency in the SEPs may indicate a positioning effect. In some embodiments, the EPDD 140 identifies a particular nerve structure or body region affected by positioning effect based on the SEPs. The EPDD 140 of some embodiments may further recommend actions to ameliorate the positioning effect by recommending changes in position.

In various embodiments, the stimulating electrode 122 may be incorporated into the EPDD 140, coupled to the EPDD 140, or attachable, directly or indirectly to the EPDD 140. According to an exemplary embodiment, the EPDD 140 sequentially stimulates peripheral nerves via the stimulating electrode 122 while recording the SEPs via the recording electrode 112. According to an exemplary embodiment, the EPDD 140 includes an output operable to couple to the stimulating electrodes 122. The recording electrodes 112 of various embodiments may be incorporated into the EPDD 140, coupled to the EPDD 140, or attachable, directly or indirectly to the EPDD 140. According to an exemplary embodiment, the EPDD 140 includes an input operable to couple the EPDD 140 to the recording electrode 112.

In an exemplary embodiment, SEPs are returned to the EPDD 140 as electrical signals recorded by the recording electrodes 112. In various embodiments, the EPDD 140 may include standard circuitry components, such as, e.g., but not limited to, electric stimulators, pre-amplifiers, amplifiers and/or computer components, etc., to control stimulation and process the return signals. According to an exemplary embodiment, the response to several stimuli is averaged together to reduce noise in the signal. In some embodiments, proprietary or third party software is used in signal processing to improve the signal-to-noise ratio and reduce the number of stimuli required to obtain a clean signal. In some embodiments, the software is stored in memory on the EPDD 140 and executed by a processor in the EPDD 140.

According to an exemplary embodiment, software, for example, software stored in the EPDD 140, is also used to analyze signals and determine when warnings and alerts are appropriate. In various embodiments, the EPDD 140 sends signals to the display unit 160 to display warnings and alerts when appropriate.

The display unit 160 may display various information on a graphical user interface (GUI), such as, for example, but not limited to, biographical information of a patient, suggested locations of electrodes, stimulation parameters, areas being stimulated and recorded, baseline and current signal traces, historical trends in signals, relevant changes in signals, location of signal changes, quality of recorded signals, position of electrodes, alerts due to significant changes in signals, and proposed movements to mitigate detrimental signal changes. In addition, the display unit 160 may include an input user interface, which includes, for example, a touchscreen, buttons, and/or control inputs. According to some embodiments, the input user interface allows an operator to set up the initial monitoring layout and interact with the display unit 160 during monitoring to add additional information, view information in a different format, or respond to alerts. In some embodiments, the display unit 160 may allow override of a change in signal by an anesthesiologist or other medical personnel, etc., when a signal change is related to a change in dose of anesthetic agent or some other event unrelated to positioning effect.

The system 100 of various embodiments, such as any of the embodiments described above, may include one or more features intended to automate and reduce the complexity of the system. Specifically, the system 100 of various embodiments includes features intended to configure the system 100 for safe and effective use by non-experts. Various exemplary features are described below.

Peripherals: Electrodes and Cables

Figure 3A:
FIG. 3A depicts a schematic top view of one embodiment of a recording electrode.
Figure 3B:
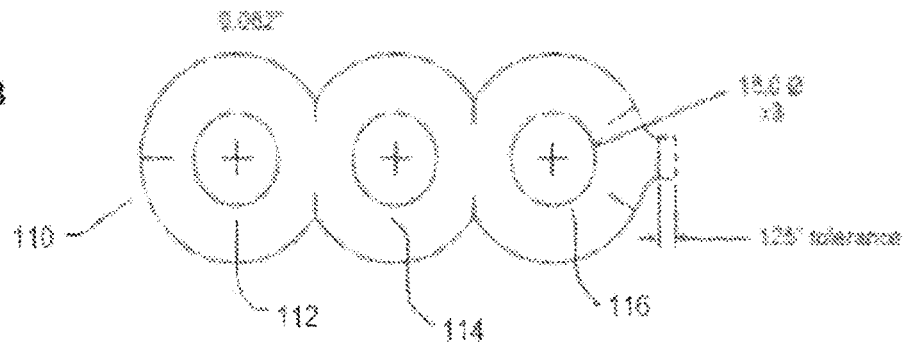
FIG. 3B depicts a schematic bottom view of the recording electrode embodiment of FIG. 3A.

FIG. 3 provides a schematic top view (3A) and bottom view (3B) of one embodiment of a recording site electrode 110 in accordance with the present disclosure. As shown, the recording site electrode 110 has three conductive pads, enabling the incorporation of a recording electrode 112, a reference electrode 114, and a ground electrode 116 into a single electrode unit. Advantageously, by including a ground electrode 116 in the single electrode unit, the system is provided with a plurality of distributed grounds. For example, in some embodiments, some or all of the peripheral recording sites have a ground electrode positioned distal to the recording and reference electrodes. That is, at each of various peripheral recording sites, a ground electrode is present and positioned between an EPDD input and the recording and reference electrodes. In other embodiments, the ground electrode may be positioned on the other side of the recording and reference electrodes. The distributed ground electrodes 116 of some embodiments will shunt the stimulus artifact away from the recording electrodes 112 and minimize the amount of stimulus that reaches the amplifier, thereby allowing for more accurate measurement of the waveform. The distributed ground 116 of some embodiments minimizes or eliminates the need for an individual, such as technologist, to perform troubleshooting of stimulus artifact reduction.

Additionally, compared to currently used systems, this combined electrode configuration, with more than one electrode included on a single electrode unit, can substantially reduce the number of electrodes that need to be prepared and placed on a patient's body. For example, in one embodiment, full body monitoring requires the placement of six recording site electrodes 110: one on the forehead, one on the C5, one on each of the two Erb's points, and one on each of the Popliteal Fossa. In currently performed methods of monitoring, the same full body monitoring may require the placement of fifteen or more recording electrodes. In some embodiments of the instant technology, there can be three electrode types provided in a kit for use with an EPDD. In addition to the recording site electrode 110 provided with three conductive pads, one recording site electrode with two conductive pads is provided, for example, for acquisition at the C5 position; such a recording site electrode may include a recording electrode and a ground electrode. One recording site electrode with one conductive pad is also provided, for example, for placement on the forehead; this single padded electrode can function as a reference electrode for the C5 electrode. In some embodiments, proper placement of the various electrodes may be facilitated by the presence of pictorial instructions on the graphical user interface (GUI). The GUI display will be discussed in more detail further below.

In addition to the integration of multiple conductive pads and electrodes into one electrode unit, the electrodes (e.g., recording site electrodes 110) of various embodiments can be wet gel electrodes. Wet gel electrodes are used in some clinical applications but are not believed to have been used before in evoked potential detection. Wet gel electrodes ensure maximum skin contact and rapidly reduce skin impedance such that the need for careful skin preparation is minimized. In various embodiments of the system 100, the stimulating site electrodes 120 and the recording site electrodes 110 are disposable, configured for single use, and biocompatible for use on intact skin. In some embodiments, an adhesive foam surrounds the conductive portion of each of the stimulating site electrodes 120 and recording site electrodes 110. The adhesive foam of some embodiments facilitates simple and secure coupling of the electrodes 110, 120 to the patient.

In some embodiments of the system 100, features as described herein can be included to minimize the amount of noise in the system—a task that is often currently performed by a surgical technician. In some embodiments, specialized cables are used to connect the EPDD 140 to the electrodes 110, 120. A photograph of four non-limiting example embodiments of such cables is provided in FIG. 4. Each cable 130a, 130b, 130c, 130d includes an inner conducting wire, which transmits the signal; the inner wire is surrounded by a tubular insulating layer, then surrounded by a tubular conducting shield, then another layer of insulation and shielding. The outermost conducting shield is grounded, protecting the inner conducting shield from electromagnetic interference caused by outside sources. Such a cable, referred to herein as a triaxial shielded cable, minimizes noise picked up from electrical noise generators such as power cables, patient warming devices, and other electronic surgical instrumentation. In various embodiments, the inclusion of triaxial shielded cables 130a, 130b, 130c, 130d in the system 100 eliminates the number of cables needed by at least a factor of two and obviates or minimizes the need to twist the cable.

Figure 4:
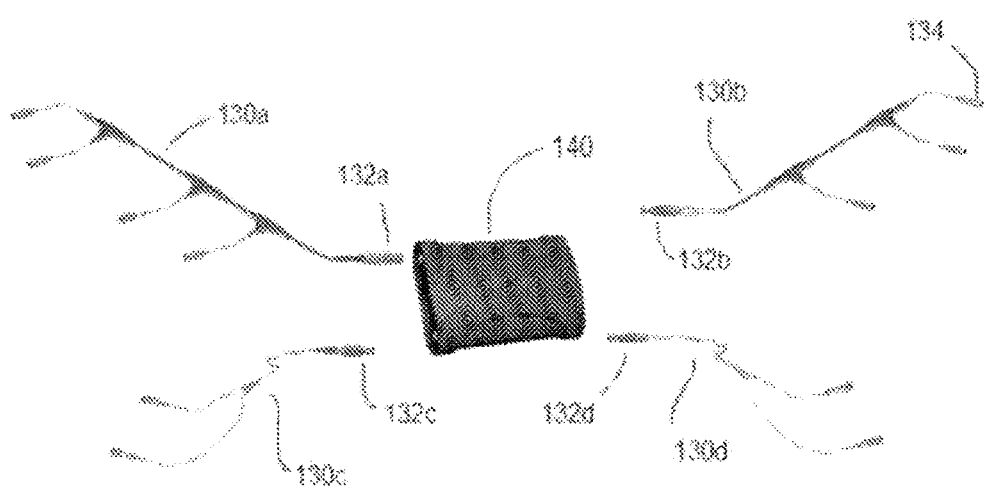
FIG. 4 is a photograph of an evoked potential detection device and associated cables, in accordance with one embodiment disclosed herein.
Figure 5A:
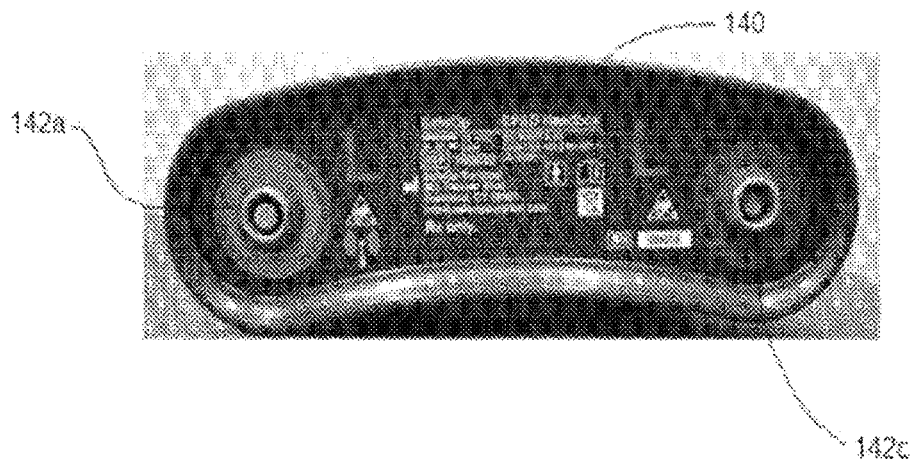
FIG. 5A depicts a left side view of the evoked potential detection device embodiment of FIG. 4.
Figure 5B:
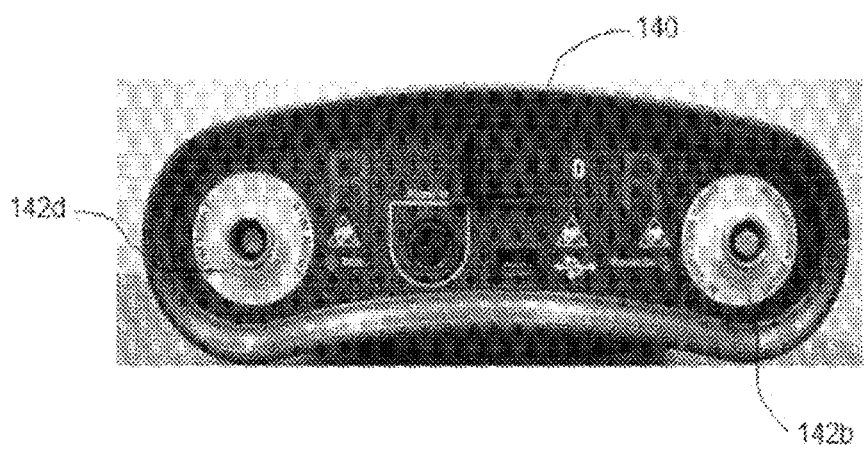
FIG. 5B depicts a right side view of the evoked potential detection device embodiment of FIG. 4.

A photograph of one embodiment of an EPDD 140 is also provided in FIG. 4. Left and right side views of said EPDD embodiment are shown in FIGS. 5A and 5B, respectively. As shown in FIG. 4, in an exemplary embodiment, each cable 130 is unique with one cable configured for each of the following: right side stimulation 132d, right side acquisition 132b, left side stimulation 132c, and left side acquisition 132a. In some embodiments, each cable 130a, 130b, 130c, 130d is provided with an electrical connector 132a, 132b, 132c, 132d, respectively. Each electrical connector 132 is configured to electrically and mechanically connect a cable 130 to one or more ports 142 in the EPDD 140. In some embodiments, each electrical connector 132 is a keyed connector with specificity to its shape such that it fits in one port in the EPDD 140 and one port only. For example, in the depicted embodiment, each electrical connector 132a, 132b, 132c, 132d is a keyed connector sized and shaped to fit exclusively into the proper respective port 142a, 142b, 142c, 142d, such that, for example, the cable for left side acquisition is inserted into the designated left side acquisition port. Such specificity in the connection may help reduce errors, particularly when the system 100 is utilized by non-expert users.

Additionally or alternatively, in some embodiments, each connector 132 makes an audible snapping sound when it securely connects to a port 142 to provide an audible indication that it is properly attached. In some embodiments, each connector 132 and each port 142 are color coded to provide a visual indication of the appropriate configuration of cables 130 in the ports 142. Other indicators may also be included to facilitate ease of system set-up and to limit errors.

In an exemplary embodiment, an anesthesiologist, surgical nurse, and/or other member of the surgical team may be able to connect all the electrodes 110, 120 and cables 130 to the EPDD 140 in five minutes or less; in other embodiments, the system 100 can be fully connected by such personnel in 2 minutes or less.

Figure 6:
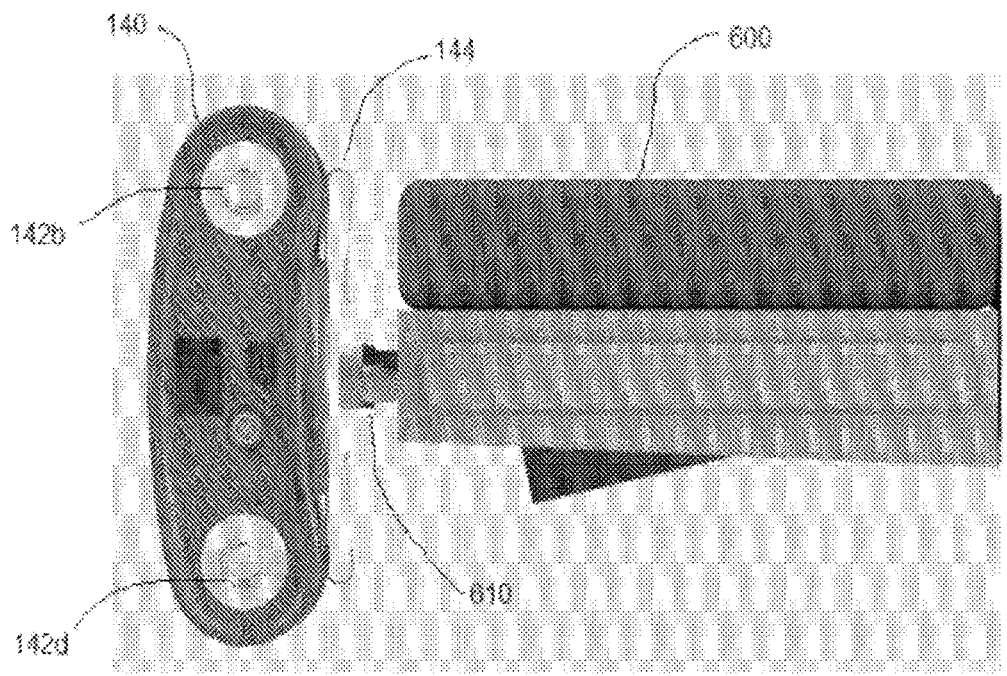
FIG. 6 depicts another right side view of the evoked potential detection device embodiment of FIG. 4 with an embodiment of a surgical table.

In order to facilitate ease of use by any surgical team member, in some embodiments of the system 100, the EPDD 140 includes an attachment mechanism, such as, for example, a clip, strap, hook, etc. for attachment to an existing surgical room structure, instrument, or apparatus. The attachment mechanism of various embodiments may be secured to the EPDD 140 via molding, adhesives, screws, or other hardware, or the like. One embodiment of an attachment mechanism is visible in the EPDD embodiment of FIG. 6. In some embodiments, the attachment mechanism is configured to securely but non-permanently attach the EPDD 140 to a surgical table 600. For example, in some such embodiments, the EPDD 140 includes a hook, clip, or strap sized, shaped, and positioned to securely but non-permanently attach to the side railing of a surgical table 600. Advantageously, a removable EPDD 140 can travel with a patient from a surgical table, to a post-op bed, a hospital bed, a wheelchair, etc. As shown in FIG. 6, the EPDD 140 of some embodiments includes a reversible mount 144 lacking in orientation. In such embodiments, the mount 144 enables the EPDD 140 to attach to a surgical table 600 or other structure in at least two orientations—for example, the EPDD 140 of FIG. 6 can attach with a top-side oriented upwardly and the EPDD 140 of FIG. 6 can alternatively attach with a bottom-side oriented upwardly. Advantageously, in such embodiments, if a patient connected to the EPDD 140 needs to be flipped, for example, from the patient's back side to the patient's front side, the cables need not be disconnected from the patient or the EPDD 140; rather, the orientation of the EPDD 140 can be flipped with the orientation of the patient. Such a feature simplifies setup and usage of a monitoring system 100.

Data Acquisition, Processing, and Presentation

Various embodiments of the system 100 also include software that facilitates the automation of the system 100. Such software may be stored within memory and executed by a processor within the system 100. In various embodiments, the memory and processor are components of a computer, and in at least some such embodiments, the EPDD 140 forms part of, is coupled via a wired or wireless connection to, and/or includes said computer. Additionally, in some embodiments, the system 100 includes one or more user interfaces to receive inputs from a user and provide outputs to the user. Such user interfaces may form part of the computer or may be in electrical or wireless communication with the computer. The user interfaces of some embodiments further facilitate the automation of the system 100. A discussion of example hardware components, which may in some embodiments be used to implement exemplary functionality and methods will be disclosed first. The functionality and methods of the system 100, as encoded for in the software and as presented to the user through the user interface(s), will follow thereafter.

Components/Structure

Figure 2:
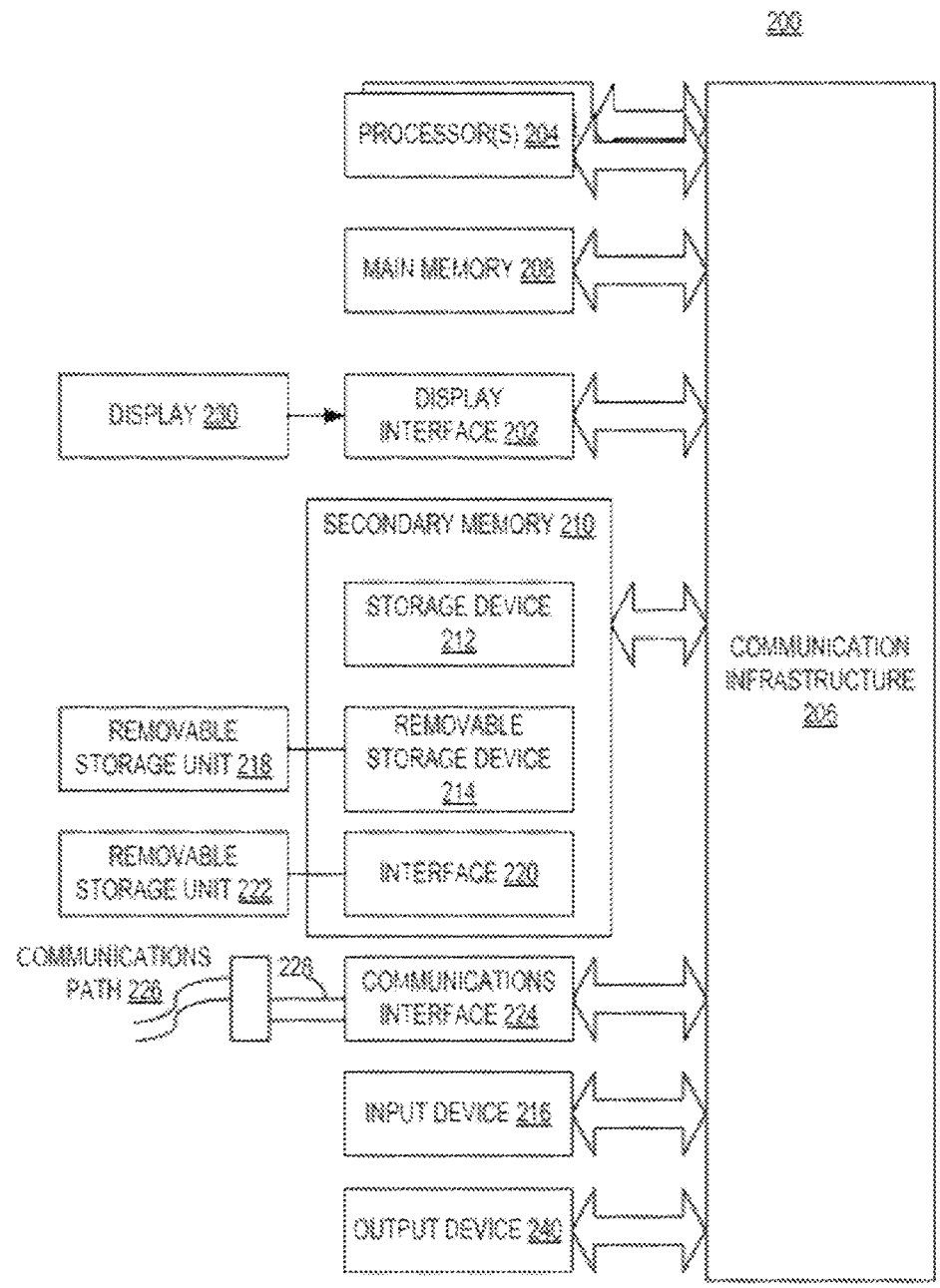
FIG. 2 depicts a functional block diagram of one embodiment of a computer system that may be used in association with, in connection with, and/or in place of any embodiment of the systems and components described herein.

FIG. 2 depicts a block diagram of one example embodiment of a computer system that may form part of any of the systems described herein. Specifically, FIG. 2 illustrates an example computer 200, which may run an operating system such as, for example, MICROSOFT® WINDOWS® NT/98/2000/XP/CE/7/VISTA/RT/8, etc. available from MICROSOFT® Corporation of Redmond, Wash., U.S.A., SOLARIS® from SUN® Microsystems of Santa Clara, Calif., U.S.A., OS/2 from IBM® Corporation of Armonk, N.Y., U.S.A., iOS or Mac/OS from APPLE® Corporation of Cupertino, Calif., U.S.A., or any of various versions of UNIX® (a trademark of the Open Group of San Francisco, Calif., USA) including, e.g., LINUX®, HPUX®, IBM AIX®, and SCO/UNIX®, or Android® from Google®, Inc. of Mountain View, Calif., U.S.A., etc. Such operating systems are provided for example only; the system embodiments described herein may be implemented on any appropriate computer system running any appropriate operating system.

Other potential components of the system 100, such as, for example, a computing device, a communications device, a personal computer (PC), a laptop computer, a tablet, a mobile device, client workstations, thin clients, thick clients, proxy servers, network communication servers, remote access devices, client computers, server computers, routers, web servers, data, media, audio, video, telephony or streaming technology servers, etc., may also be implemented using a computer such as that shown in FIG. 2.

The computer system 200 may include one or more processors, such as processor(s) 204. The processor(s) 204 may be connected to a communication infrastructure 206 (for example, a communications bus, cross-over bar, or network, etc.). Various software embodiments may be described in terms of this example computer system. After reading this description, it will become apparent to a person skilled in the relevant art(s) how to implement the described methods using other computer systems and/or architectures.

Computer system 200 may include a display interface 202 to forward graphics, text, and other data, etc., from the communication infrastructure 206 for display on the display unit 230.

The computer system 200 may also include, e.g., but may not be limited to, a main memory 208, random access memory (RAM), and a secondary memory 210, etc. The secondary memory 210 may include, for example, (but may not be limited to) a hard disk drive 212 and/or a removable storage drive 214, representing a floppy diskette drive, a magnetic tape drive, an optical disk drive, a magneto-optical disk drive, a compact disk drive CD-ROM, a digital versatile disk (DVD), a write once read many (WORM) device, a flash memory device, etc. The removable storage drive 214 may read from and/or write to a removable storage unit 218 in a well-known manner. Removable storage unit 218 may represent, for example, a floppy disk, a magnetic tape, an optical disk, a magneto-optical disk, a compact disk, a flash memory device, etc. which may be read from and written to by removable storage drive 214. As will be appreciated, the removable storage unit 218 may include a computer usable storage medium having stored therein computer software and/or data.

In alternative exemplary embodiments, secondary memory 210 may include other similar devices for allowing computer programs or other instructions to be loaded into computer system 200. Such devices may include, for example, a removable storage unit 222 and an interface 220. Examples of such may include a program cartridge and cartridge interface (such as, e.g., but not limited to, those found in some video game devices), a removable memory chip (such as, e.g., but not limited to, an erasable programmable read only memory (EPROM), or programmable read only memory (PROM) and associated socket, and other removable storage units 222 and interfaces 220, which may allow software and data to be transferred from the removable storage unit 222 to computer system 200.

Computer 200 may also include an input device 216 such as, for example, a mouse or other pointing device such as a digitizer, a touchscreen, a microphone, a keyboard, and/or other data entry device. Computer 200 may also include output devices 240, such as, for example, a display 230 and/or display interface 202. Computer 200 may include input/output (I/O) devices such as a communications interface 224, a cable 228, and/or a communications path 226, etc. These devices may include but are not limited to a network interface card and modems. The communications interface 224 may allow software and data to be transferred between the computer system 200 and external devices. Examples of a communications interface 224 include, for example, a modem, a network interface (such as, e.g., an Ethernet card), a communications port, a Personal Computer Memory Card International Association (PCMCIA) slot and card, etc. Software and data transferred via the communications interface 224 may be in the form of signals 228 which may be electronic, electromagnetic, optical, or other signals capable of being received by the communications interface 224. These signals 228 may be provided to the communications interface 224 via, for example, a communications path 226 such as a channel. This channel 226 may carry signals 228, for example propagated signals, and may be implemented using, for example, wire or cable, fiber optics, a telephone line, a cellular link, a radio frequency (RF) link and other communications channels, etc.

In various embodiments described herein, wired networks may include any of a wide variety of well-known means for coupling voice and data communications devices together. In various embodiments described herein, wireless network types may include, but are not limited to, for example, code division multiple access (CDMA), spread spectrum wireless, orthogonal frequency division multiplexing (OFDM), 1G, 2G, 3G, or 4G wireless, Bluetooth, Infrared Data Association (IrDA), shared wireless access protocol (SWAP), "wireless fidelity" (Wi-Fi), WIMAX, and other IEEE standard 802.11-compliant wireless local area network (LAN), 802.16-compliant wide area network (WAN), and ultra-wideband (UWB) networks, etc.

Some embodiments may include or otherwise make reference to WLANs. Examples of a WLAN may include a shared wireless access protocol (SWAP) developed by Home radio frequency (HomeRF), and wireless fidelity (Wi-Fi), a derivative of IEEE 802.11, advocated by the wireless Ethernet compatibility alliance (WECA). The IEEE 802.11 wireless LAN standard refers to various technologies that adhere to one or more of various wireless LAN standards. An IEEE 802.11 compliant wireless LAN may comply with any of one or more of the various IEEE 802.11 wireless LAN standards including, for example, wireless LANs compliant with IEEE std. 802.11a, b, d, g, or n, such as, e.g., but not limited to, IEEE std. 802.11 a, b, d, g, and n (including, e.g., but not limited to IEEE 802.11g-2003, etc.), etc.

Some embodiments described herein are directed to the apparatuses and/or devices for performing the operations described herein. Such an apparatus may be specially constructed for the desired purposes, or it may comprise a general purpose device selectively activated or reconfigured by a program stored in the device to perform the specialized purpose.

Other embodiments described herein are directed to instructions stored on a machine-readable medium, which may be read and executed by a computing platform to perform operations described herein. A machine-readable medium may include any mechanism for storing or transmitting information in a form readable by a machine (e.g., a computer). For example, an exemplary machine-readable storage medium may include: read only memory (ROM); random access memory (RAM); magnetic disk storage media; optical storage media; magneto-optical storage media; flash memory devices; other exemplary storage devices capable of storing electrical, optical, acoustical, or other form of propagated signals (e.g., carrier waves, infrared signals, digital signals, etc.) thereon, and others. Computer programs (also called computer control logic), may include object oriented computer programs, and may be stored in main memory 208 and/or the secondary memory 210 and/or removable storage units 214, also called computer program products. Such computer programs, when executed, may enable the computer system 200 to perform the features of the present invention as discussed herein. In particular, the computer programs, when executed, may enable the processor or processors 204 to provide a method to control and/or manage operation of an EPDD according to an exemplary embodiment. Accordingly, such computer programs may represent controllers of the computer system 200.

Another exemplary embodiment is directed to a computer program product comprising a computer readable medium having control logic (computer software) stored therein. The control logic, when executed by the processor 204, may cause the processor 204 to perform functions described herein. In other embodiments, various functions described herein may be implemented primarily in hardware using, for example, but not limited to, hardware components such as application specific integrated circuits (ASICs), or one or more state machines, etc. Implementation of the hardware state machine so as to perform the functions described herein will be apparent to persons skilled in the relevant art(s). In some embodiments, described functions may be implemented using one or a combination of any of hardware, firmware, and software, etc.

As used herein, the terms "computer program medium" and "computer readable medium" may generally refer to media such as, e.g., but not limited to removable storage drive 214, a hard disk installed in hard disk drive and/or other storage device 212, and signals 228, etc. These computer program products may provide software to computer system 200. An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Unless specifically stated otherwise, as apparent from the following discussions, it may be appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

According to an exemplary embodiment, exemplary methods set forth herein may be performed by an exemplary one or more computer processor(s) adapted to process program logic, which may be embodied on an exemplary computer accessible storage medium, which when such program logic is executed on the exemplary one or more processor(s) may perform such exemplary steps as set forth in the exemplary methods.

Methods and Functions

Figure 7:
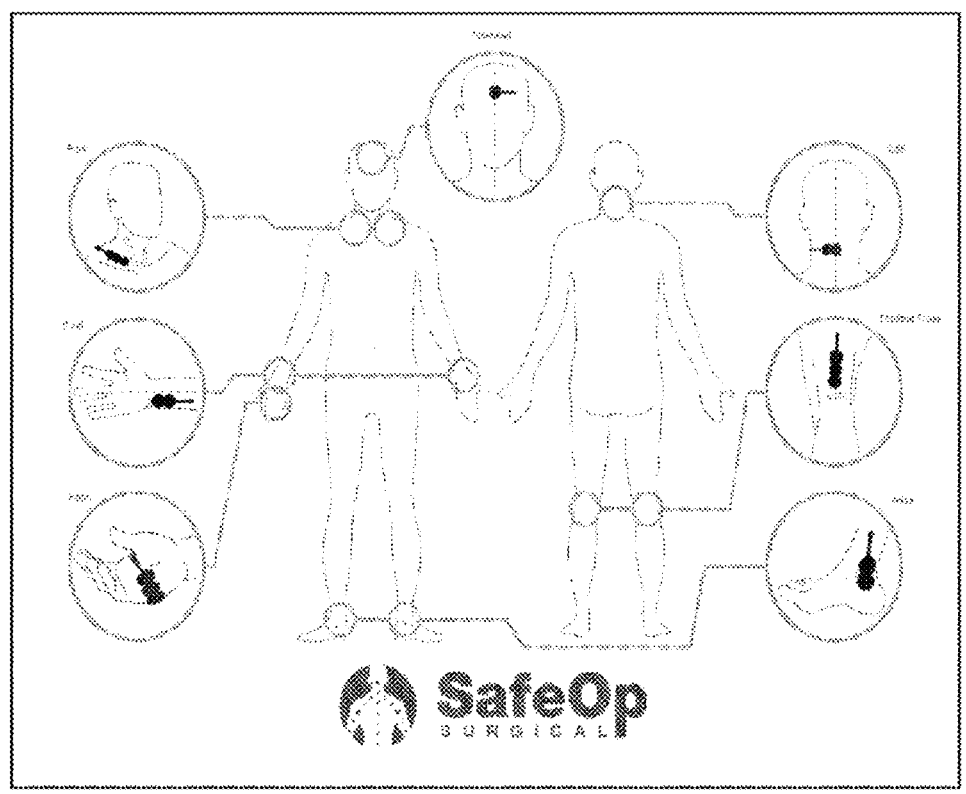
FIG. 7 depicts one embodiment of a user interface in accordance with embodiments disclosed herein.

In some embodiments, the system 100 facilitates setup of the system by a non-expert by providing visual cues and instructions during the setup process. For example, as shown in FIG. 7, in some embodiments, the display 230 includes a graphical user interface, which may be configured to display pictorial instructions of where to place electrodes on a patient's body. Such an image may appear, for example, upon powering up the computer 200, upon indicating via an input device 216 that monitoring of a new patient is commencing, or upon receiving a signal that a cable has been connected to the EPDD. In FIG. 7, each circle represents the recommended location of an electrode.

Additionally or alternatively, in some embodiments, the system 100 facilitates the acquisition of reliable signals by non-experts by automatically testing electrode impendence prior to, or during, patient monitoring. An exemplary method for automatically testing electrode impendence is provided in FIG. 8. Such a method may be performed, for example, by a computer 200. In some embodiments, the computer 200 is housed within the EPDD 140. In some embodiments of the method 800, the computer 200 receives an input to start testing or monitoring (block 802). The computer 200 may receive the input from a user via an input device 216, such as, for example, a touchscreen. In some embodiments, the input device is external to the computer 200 and the input from the input device is transmitted to the computer 200, for example, via one or more communication buses and cables or via a wireless transmitter.

At block 804, the computer of some embodiments detects impedance of an acquisition electrode 110, and at block 806, the computer 200 determines if the impedance level is acceptable. For example, in some embodiments, the computer 200 compares the detected impedance level to an acceptable threshold impedance level. If the detected impedance level is equal to or below the acceptable threshold impedance level, the detected impedance may be determined to be acceptable. If the detected impedance level is above the acceptable threshold impedance level, the detected impedance may be determined to be unacceptable.

In some embodiments, if the detected impedance is acceptable, the computer 200 proceeds to block 808. In such embodiments, if the detected impedance is acceptable, the computer 200 transmits an output to a user interface providing signals/instructions to display the impedance of a particular electrode as acceptable. In some embodiments, if the detected impedance is unacceptable, the computer 200 proceeds to block 810. In such embodiments, if the detected impedance is unacceptable, the computer 200 transmits an output to a user interface providing signals/instructions to display the impedance of a particular electrode as unacceptable. The user interface of some embodiments is a display 230, such as a touchscreen or other screen. In some embodiments, the user interface is external to the computer 200. In some such embodiments, the output is transmitted to the display 230 or other user interface via one or more communication buses and cables or via a wireless transmitter.

In various embodiments, blocks 804, 806, and 808 and/or 810 are repeated sequentially or simultaneously or with partial overlap until each connected acquisition electrode has been tested and the results of the test have been displayed via a user interface.

Figure 9:
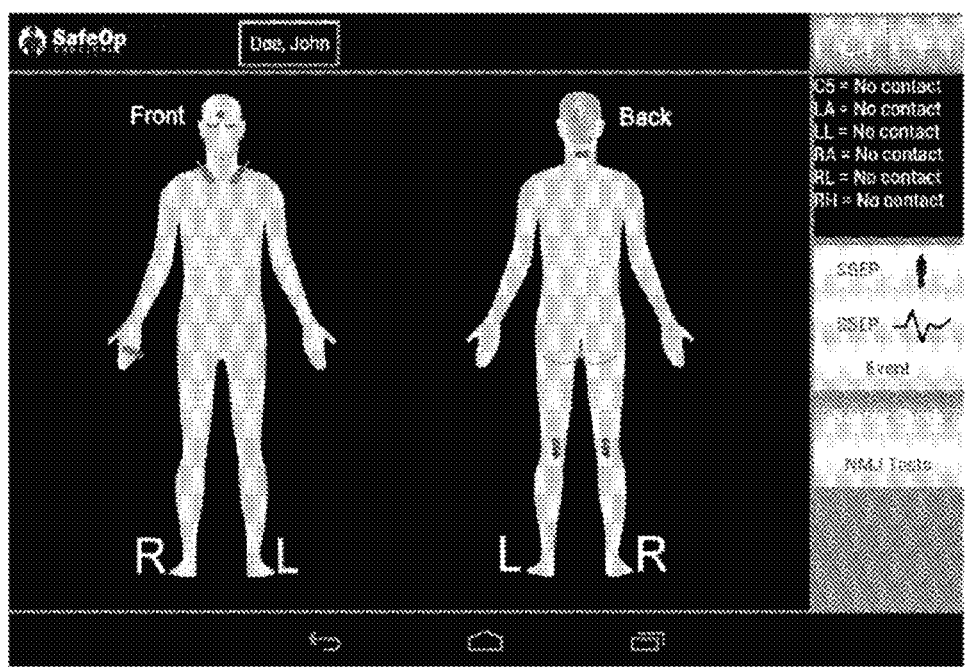
FIG. 9 depicts one embodiment of a user interface in accordance with embodiments disclosed herein.

One embodiment of the output of the user interface is provided in FIG. 9. In some embodiments of the user interface, each acquisition electrode is depicted pictorially on the body of a patient. In some such embodiments, an electrode is shown as white, gray, or black if not tested, an electrode is shown as red if it has an unacceptably high impedance, and an electrode is shown as green if the impedance level is acceptable. In the embodiment of FIG. 9, all acquisition electrodes received an unacceptable rating in the impedance testing.

Returning to FIG. 8, after the results of the impedance testing have been displayed, the computer 200 must determine whether to proceed with patient monitoring as shown at block 812. If all tested electrodes were found to be acceptable, the computer 200 of some embodiments will automatically proceed to block 814 and begin patient monitoring; in other embodiments, the computer 200 will proceed to block 814 upon receiving an instructive input from a user via an input device. If some but not all of the tested electrodes were found to be acceptable, the user will be prompted, via an input/output device, to select whether the computer 200 should proceed to patient monitoring using only the acceptable electrodes. If the user selects yes, the computer 200 will proceed to block 814 and monitor the patient using the acceptable electrodes only. If the user selects no, the computer 200 will proceed to block 816 and the startup process will be suspended so that the user can check electrode and cable connections, reapply electrodes if needed, and repeat the impedance test. The system 100 of various embodiments will not allow the user to acquire patient signals using electrodes having unacceptable impedance levels.

Once monitoring of a patient begins, the system 100 of some embodiments additionally or alternatively includes functions for facilitating the automation of data acquisition and analysis. For example, in some embodiments, the EPDD 140 is programmed with a default stimulation level; in some such embodiments, the EPDD 140 automatically adjusts the stimulation level as needed. For example, in some embodiments, during the application of stimulations, the EPDD 140 monitors the size of evoked potential signals it receives as inputs from the recording electrodes 110. If the resultant evoked potentials do not increase in size with increased stimulation, the EPDD 140 maintains this stimulation level (i.e. commonly referred to as supramaximal stimulation) or a value slightly above this level, such as, for example, 5% above this level, to ensure total stimulation of the nerve. Conversely, if the resultant evoked potentials are too small for reliable processing, for example, if the evoked potentials increase in size with increasing stimulation, the EPDD 140 increases the stimulation level, for example, until the responses no longer increase in size.

In some embodiments, the system 100 includes one or more means of automatically managing and minimizing noise contamination within the signal in order to automatically generate reliable data. For example, in some embodiments, the system 100 is configured to automatically detect when a high-noise generating device, such as an ESU, is in operation. In some embodiments, the system 100 temporarily suspends data acquisition and/or grounds all received signals during the operation of an ESU. ESUs cut and cauterize tissue by applying electrical energy from a radiofrequency (RF) generator to the tip of the ESU. Thus, in an exemplary embodiment of the system 100, the EPDD 140 includes an RF receiver configured to receive radio frequencies emitted from nearby devices, such as an ESU. In some embodiments, the RF receiver is included within an amplification system in the EPDD 140; for example, in some embodiments, the RF receiver is incorporated into signal amplifiers in the system. In some embodiments, when a threshold level of RF signals are detected by the RF receiver of the EPDD 140, the computer 200 suspends signal acquisition or signal processing.

In some embodiments, the computer 200 stores and executes computer signal processing and pattern recognition algorithms for the automatic characterization and classification of EPs in real-time. Implementation of this algorithm may substitute for the expert analysis typically provided by the surgical technologist and neurologist. In various embodiments, certain functionality, such as, for example, the inclusion of a shifting baseline and the reduction of data into simple categories such as "good" and "bad" allows for the production of meaningful results for non-expert users.

Figure 10:
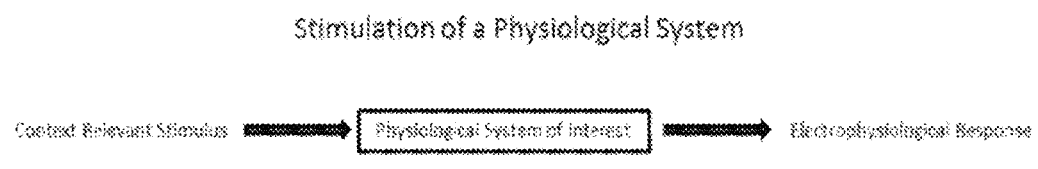
FIG. 10 depicts one embodiment of stimulation of a physiological system of interest with a context relevant stimulus.

FIG. 10 illustrates one example of a stimulation of a physiological system of interest with a context relevant stimulus. For the somatosensory system, a context relevant stimulus may be the application of an appropriate sized and shaped current pulse over a superficial nerve.

Figure 11:
FIG. 11 depicts one embodiment of a sequence of suitable stimuli applied to a physiological system of interest and the sequence of corresponding responses.
Figure 11:
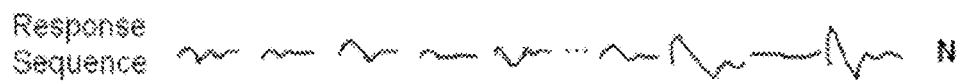

FIG. 11 illustrates an exemplary depiction of a sequence of suitable stimuli applied to a physiological system of interest and the sequence of corresponding responses. These responses are comprised of time sampled and digitized measurements of the volume conducted voltage fields created by the electrophysiological response of the physiological system of interest when evoked by the applied stimuli.

Figure 12:
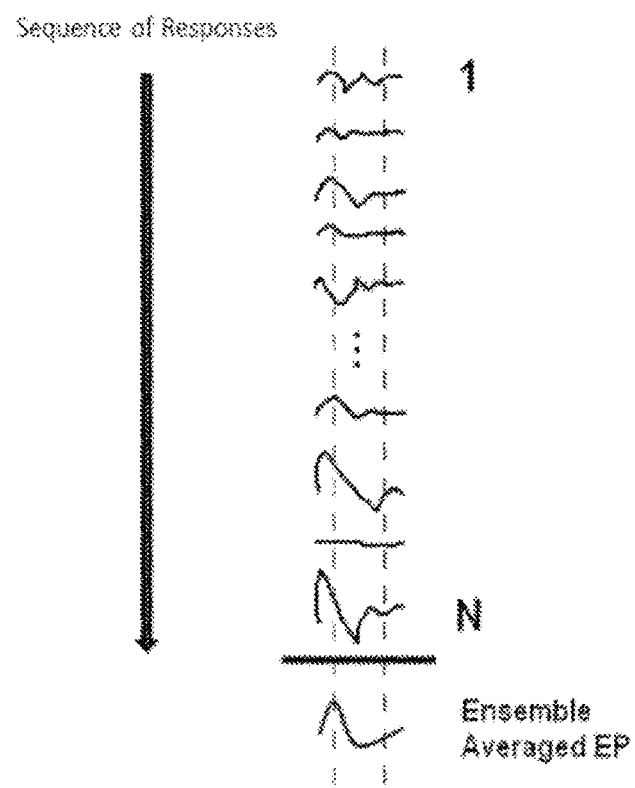
FIG. 12 depicts one embodiment of the creation of an ensemble averaged EP based on a number of responses.

FIG. 12 illustrates an exemplary depiction of the creation of an ensemble averaged EP based on a number of responses. As described above, in order to obtain a suitable signal to noise ratio, a number of responses may be ensemble averaged to create a resulting evoked potential (EP). The signal to noise ratio of the resulting EP improves as N, the number of responses averaged, increases. In an embodiment, N may range from 10 to 1000 depending on the physiological system of interest.

EPs may be processed to assess the state of the physiological system of interest. A physiological system in a normal operating mode may be considered to be in a "Good" state. If the physiological system is stressed, fatigued, or injured, the system may be considered to be in a "Bad" state. Starting with the physiological system in a Good state, detected changes in the characteristics of the EPs in a sequence of EPs can be used to predict if the physiological system is in a Good or Bad state.

Figure 13A:
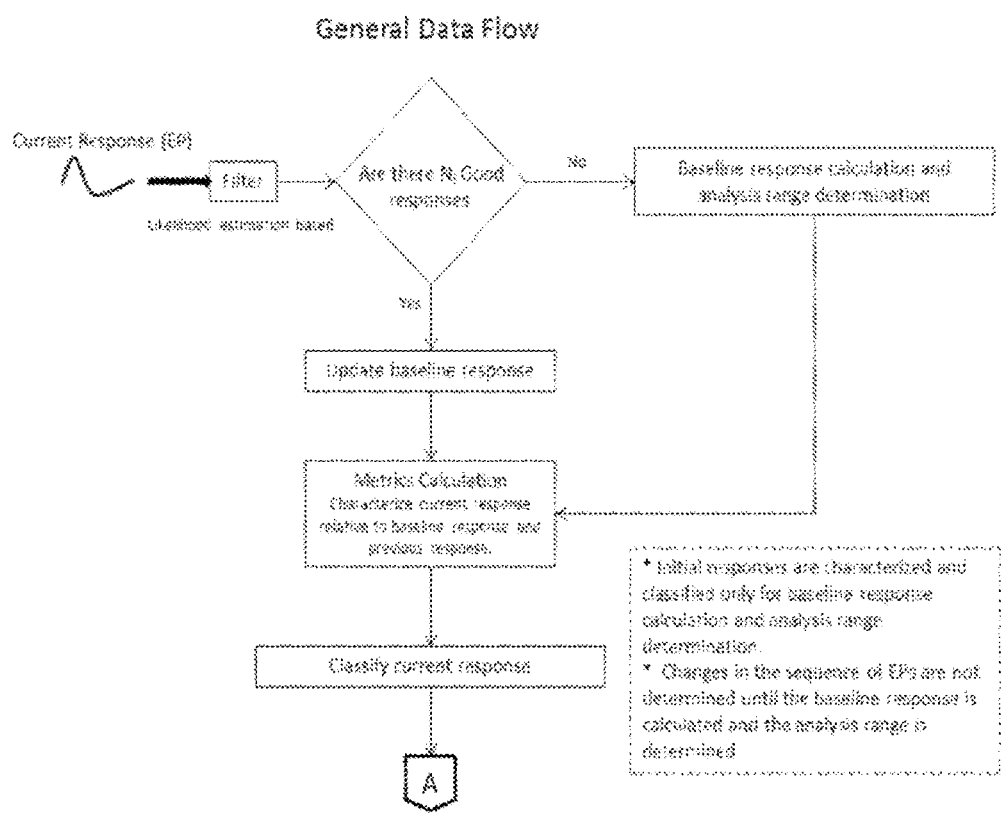
FIG. 13A depicts one embodiment of a flowchart process for acquiring and classifying EP responses.

FIG. 13A illustrates an exemplary flowchart process for acquiring and classifying EP responses. Each EP may be initially filtered to remove unwanted instrumentation noise to better present the electrophysiological response of the system of interest. The EPs may be filtered based on likelihood estimation.

If a baseline response does not exist, acquired responses may be analyzed to estimate a baseline response and to establish an analysis range. For example, if there is not $N_I$ Good responses received, where $N_I$ is a number of initial EP responses required to create a baseline response, then a baseline response may not exist. The analysis to estimate a baseline response and to establish an analysis range is further described below. If a baseline response exists, the baseline may be updated based on the current response. Updating the baseline is further described below.

Once the current baseline response is determined, the current response is then characterized relative to the current baseline and previous response. For example, characterization may be at least one of a Euclidean distance, a pseudo-correlation, a cross-correlation, or an energy ratio between the current response and current baseline. Energy ratio may be the ratio of the energy between the current response and the current baseline. The energy ratio may represent a change in size of the EP response. The current response may then be classified based on the current response's characterization.

EPs may be classified into four possible categories: Good, Bad, Undetermined and Unreliable based on the characterization. A Good classification may indicate the EP characterization corresponds with no significant waveform change. For example, when there is no positioning effect. A Bad classification may indicate the EP characterization corresponds with a signification waveform change. For example, when there is positioning effect. An Undetermined classification may indicate that the EP characterization may be of indeterminate significance. For example, the EP characterization may be insufficient for a Good classification but also insufficient for a Bad classification. For example, the EP may possibly correspond with either positioning effect or no positioning effect. An unreliable classification may indicate the EP includes too much noise to be properly characterized and classified.

Each classification may correspond with a particular threshold. The threshold may indicate how similar an EP response should be to a baseline to be considered a Good response or how dissimilar an EP response should be to a baseline to be considered a Bad response. The thresholds may be based on the characterizations of the EP responses. For example, thresholds may be based on at least one of Euclidean distance, a pseudo-correlation, a cross-correlation, or an energy ratio between an EP response and a baseline. A threshold may also indicate how much noise may be included in an EP response before the EP response is considered unreliable.

The thresholds used for classification may be determined by analyzing training data. Training data may include a plurality of EP responses known to correspond to particular classifications. Using multiple sets of thresholds determined from the analysis of training data, the current response may be classified as belonging to a category of interest based on the values of its calculated metrics.

Figure 13B:
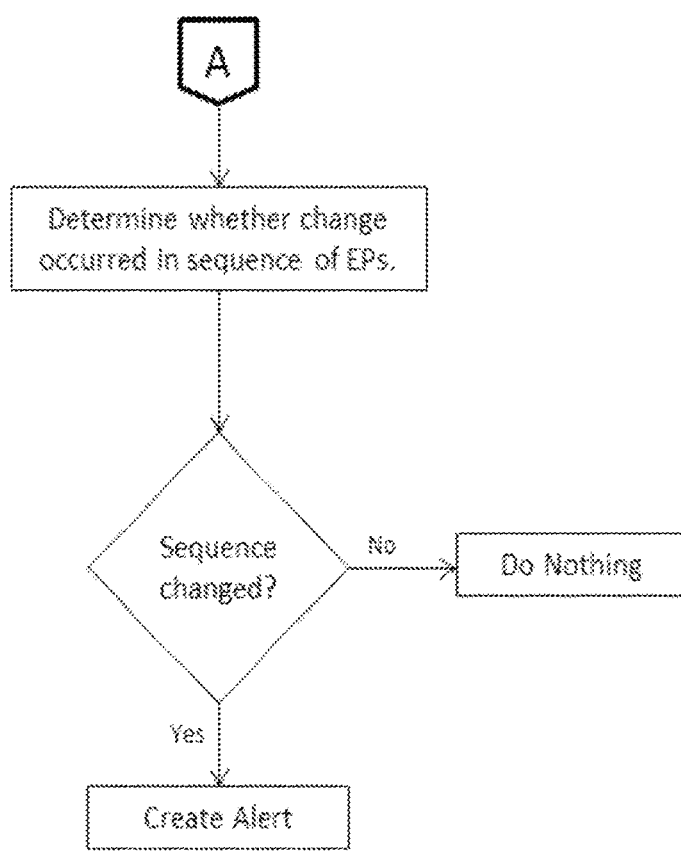
FIG. 13B depicts one embodiment of a flowchart process for determining whether a change has occurred in a sequence of EPs.

FIG. 13B illustrates an exemplary flowchart process for determining whether a change has occurred in a sequence of EPs. FIG. 13B continues from FIG. 13A. Given the sequence of classified EPs, it may be determined whether the state of the physiological system of interest has changed (either from Good to Bad or vice versa) or if the state of the physiological system of interest has not changed. If the state has changed, the system may create an alert.

Figure 14:
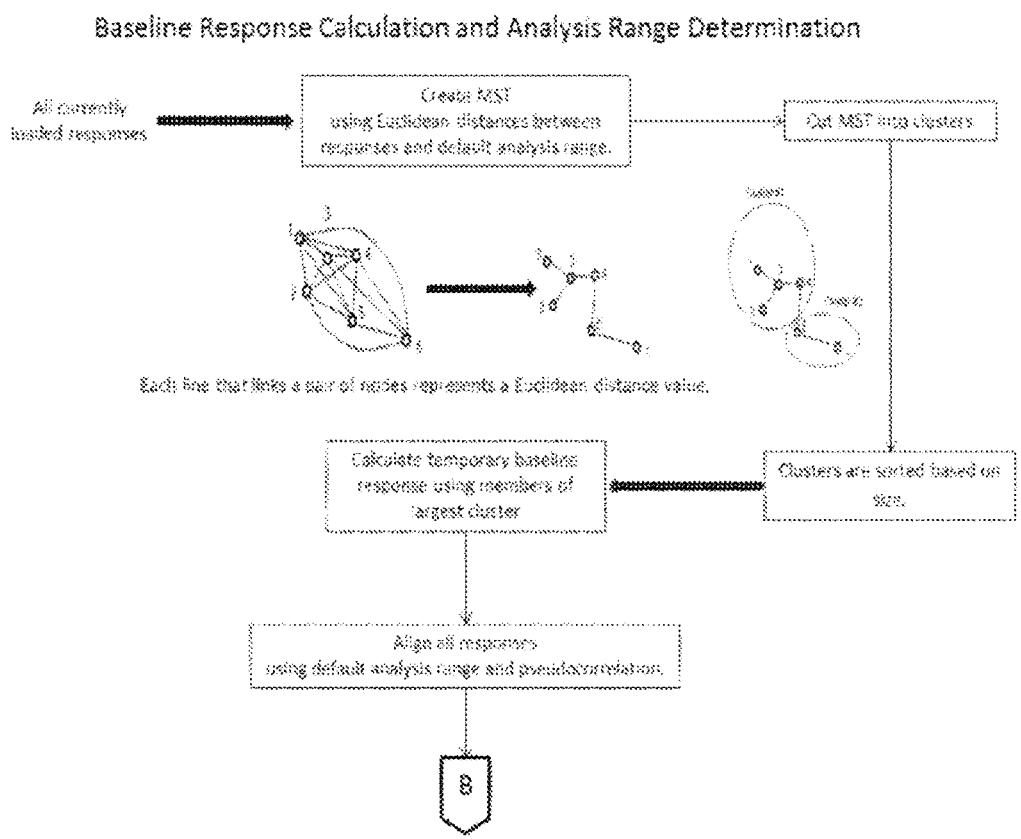
FIG. 14 depicts one embodiment of a flowchart process for calculating a baseline response.

FIG. 14 illustrates an exemplary flowchart process for calculating a baseline response. Currently loaded responses may be iteratively represented as nodes within a minimum spanning tree (MST) created using the Euclidean distances between response pairs. Each line in the MST that links pairs of responses may represent a Euclidean distance value. The currently loaded responses may be initially acquired responses. Response pairs may be combinations of any two currently loaded responses. For example, three responses may result in three response pairs. The Euclidean distance may be based on the sum of the squares of the differences between responses in each response pair or the sum of the absolute value of the differences between responses in each response pair.

The MST may be separated into clusters based on cutting lines that are greater than a threshold. The threshold may be based on the mean of the line lengths and standard deviations of the line lengths. The clusters may be sorted based on the sizes of the clusters. The size of a cluster may be the number of responses within the cluster. The cluster with the largest size may be selected so that a temporary baseline is calculated based on the responses within the cluster. All the responses within the largest cluster may be aligned using a default analysis range and pseudo-correlation. The response members of the cluster with the largest number of members may be averaged to estimate the baseline response.

Figure 15:
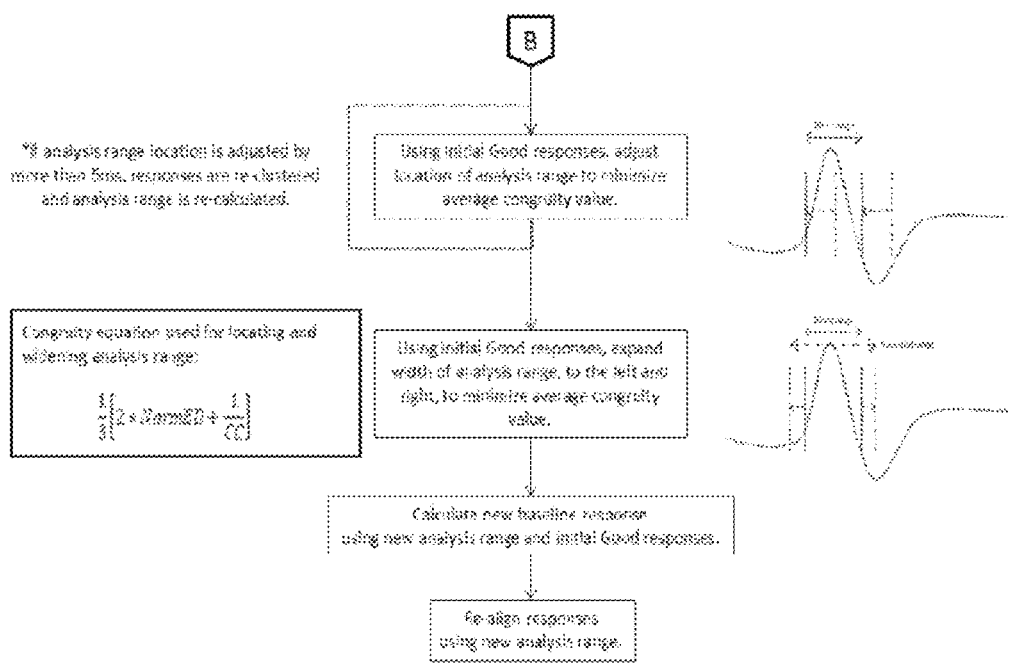
FIG. 15 depicts one embodiment of a flowchart process for determining the analysis range.

FIG. 15 illustrates an exemplary flowchart process for determining the analysis range. Initial responses are characterized and classified using initial baseline response estimates and a default analysis range. First, initial Good responses are used to locate a default width analysis range by adjusting the location of the range until a minimum congruity value is obtained. Using the initial Good responses, the width of the analysis range is then adjusted by increasing it to the left or right until a minimum congruity value is obtained. For both analysis range location and sizing, the congruity measure may be:

$$\frac{1}{3}\left[2*NormED + \frac{1}{CC}\right]$$

where NormED is a normalized Euclidean distance and CC is the cross-correlation. While not shown in FIG. 15, the calculated new baseline response may be used to re-calculate the analysis range.

Figure 16:
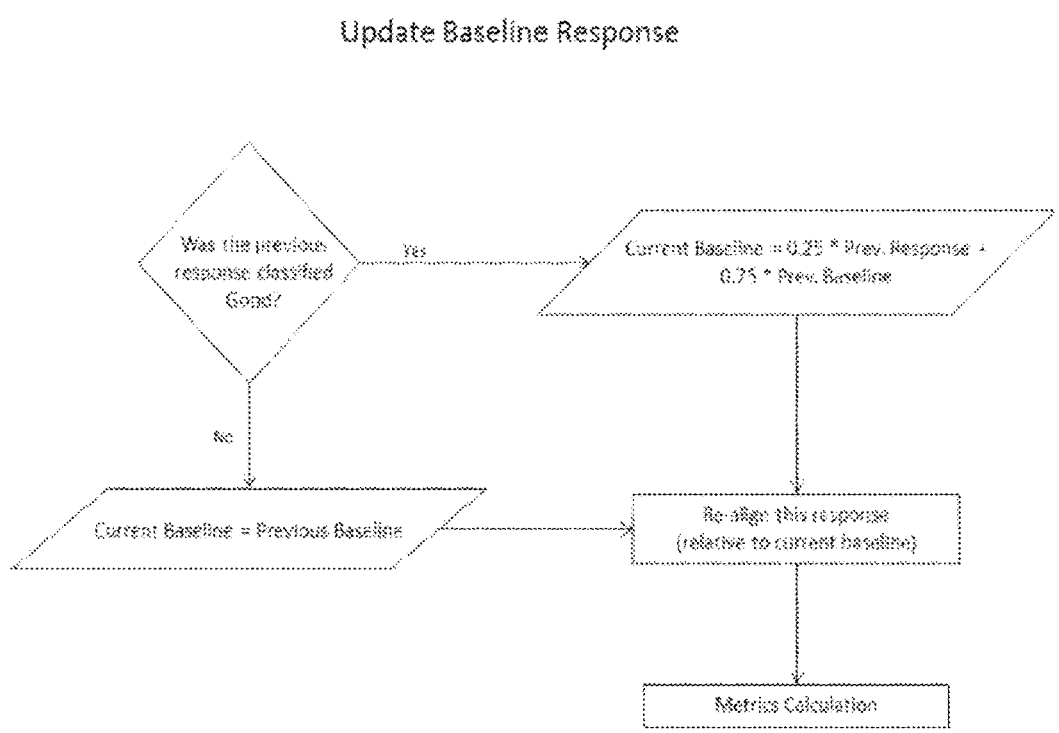
FIG. 16 depicts one embodiment of a flowchart process for updating a baseline response.

FIG. 16 illustrates an exemplary flowchart process for updating a baseline response. As shown in FIG. 16, if a previous response is classified as good, the current baseline may be recalculated based on the previous response and the previous baseline. For example, the current baseline may be set to a weighted average equal to 25% of the previous response and 75% of the previous baseline. If the previous response is not classified as good, the current baseline may remain set to the previous baseline.

Regardless of how the new current baseline is determined, the new current baseline may be used to re-align the current response relative to the new current baseline. Metric calculation may then be performed on the re-aligned response.

Figure 17:
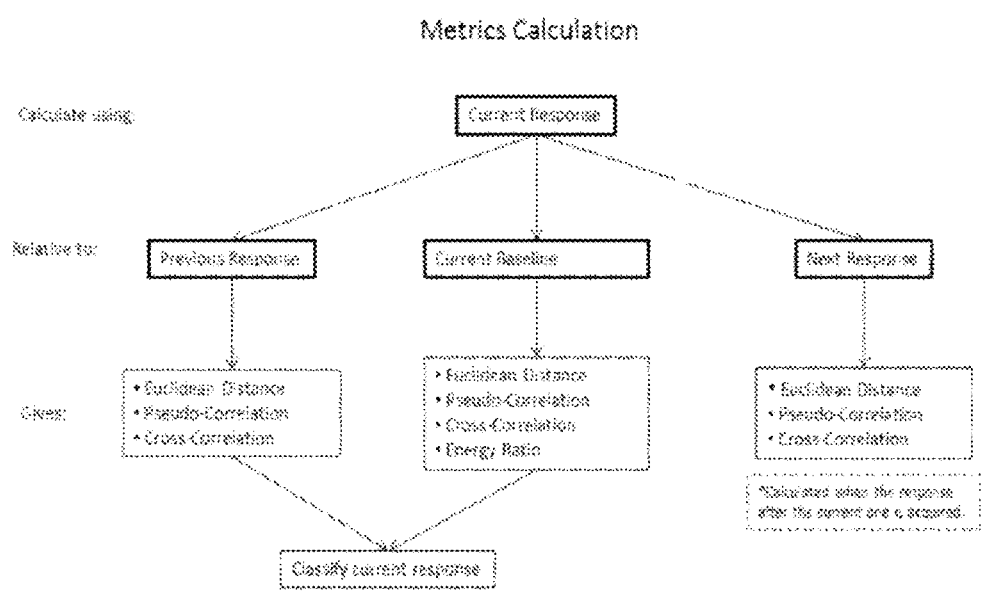
FIG. 17 depicts one embodiment of a relationship diagram in metric calculation for characterizing EPs.

FIG. 17 illustrates an exemplary embodiment of a relationship diagram in metric calculation for characterizing EPs. As shown in FIG. 17, a current response may be compared with a previous response to give a Euclidean distance between the responses, a pseudo-correlation, and a cross-correlation. A current response may be compared with a current baseline to give a Euclidean distance between the response and baseline, a pseudo-correlation, a cross-correlation, and an energy ratio. The current response may be classified based on these various results.

After a next response is acquired, the current response may also be used to give a Euclidean distance between the current response and next response, a pseudo-correlation, and a cross-correlation.

Figure 18:
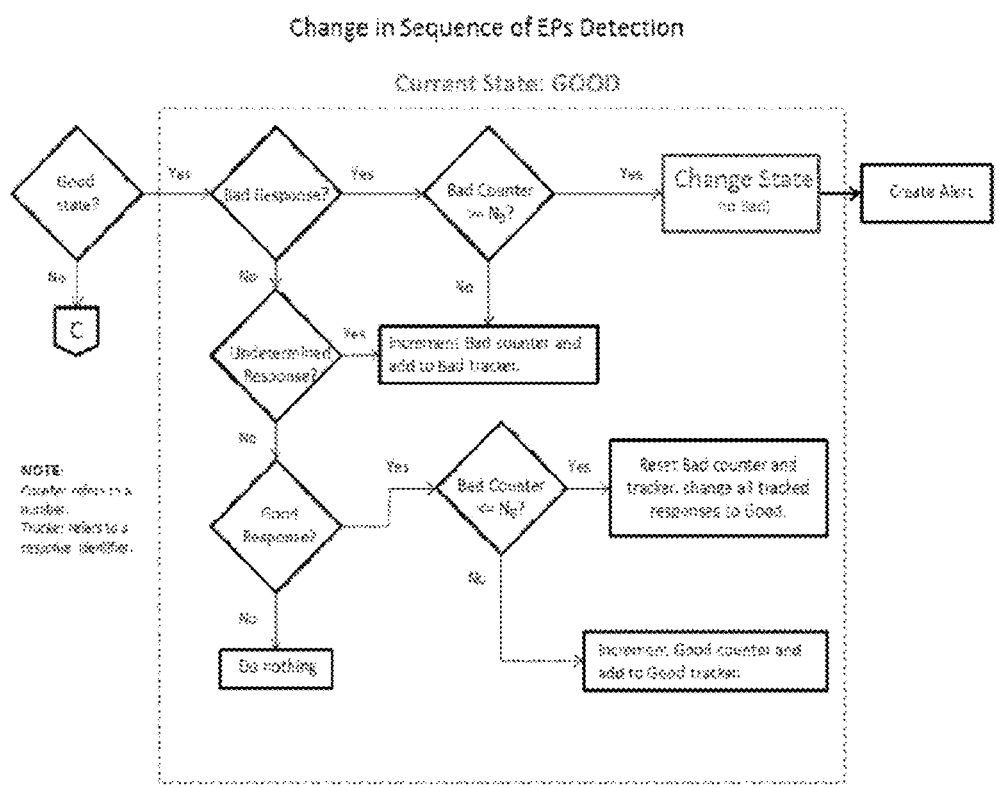
FIG. 18 depicts one embodiment of a flowchart process for a good state.

FIG. 18 illustrates an exemplary flowchart process for a good state according to an exemplary embodiment of the present invention. If a Bad response is received while in the Good state, the system may check to see if a bad counter is greater than or equal to a bad counter threshold, $N_B$. The bad counter may indicate a number of Bad responses. The bad counter threshold $N_B$ may indicate the number of Bad responses or undetermined responses to receive before the next Bad response changes the state to a bad state. The bad counter threshold $N_B$ may be set for each state depending on the physiological system of interest.

If the bad counter is greater than the bad counter threshold $N_B$, then the current state may be changed to the Bad state and an alert may be created. The alert may be conveyed to a user of the system in a variety of ways, e.g., with displaying visualizations, generating sounds, creating vibrations, etc. If the bad counter is not greater than bad counter threshold $N_B$, then the bad counter may be incremented and the Bad response added to a bad tracker. The bad tracker may track the Bad responses and Undetermined responses received.

If the response received is not a bad response, the system may check if the response received is an undetermined response. If the response received is an undetermined response, then the bad counter is also incremented and the undetermined response is added to the bad tracker.

If the response received is also not an undetermined response, the system may check if the response received is a good response. If the response received is a good response, then if the bad counter is less than or equal to the bad counter threshold $N_B$, then the bad counter is reset to zero and the bad tracker is emptied.

If the response received is also not a good response, then the system may determine that the response is an unreliable response and may ignore the response.

Based on the bad counter, the bad tracker, the good counter, and the good tracker, the system may provide different indications to a user. The system may change the color of an icon displayed so that the icon appears green when the bad counter is zero and gradually becomes redder with increasing values for the bad tracker.

Figure 19:
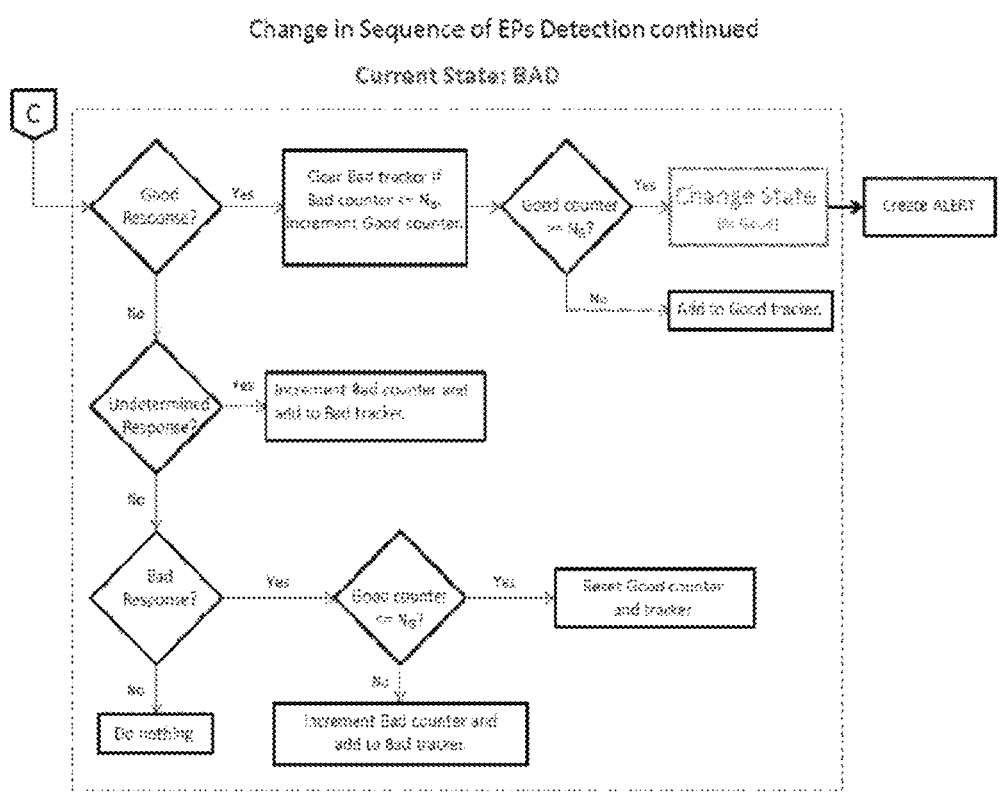
FIG. 19 depicts one embodiment of a flowchart process for a bad state.

FIG. 19 illustrates an exemplary flowchart process for a bad state according to an exemplary embodiment of the present invention. If a good response is received while in the bad state, the system may increment a good counter, and, if the bad counter is less than the bad counter threshold $N_B$, clear the bad tracker check.

The system may check to see if a good counter is greater than or equal to a good counter threshold, $N_G$. The good counter may indicate a number of good responses. The good counter threshold $N_G$ may indicate the number of good responses needed to be received to change the state to a good state. The good counter threshold $N_G$ may be set for each state depending on the physiological system of interest. If the good counter is greater than the good counter threshold $N_G$, then the current state may be changed to the good state and an alert may be created. If the good counter is not greater than good counter threshold $N_G$, then the good response may be added to a good tracker. The good tracker may track the good responses received.

If the response received is not a good response, the system may check if the response received is an undetermined response. If the response received is an undetermined response, then the bad counter is incremented and the undetermined response is added to the bad tracker.

If the response received is also not an undetermined response, the system may check if the response received is a bad response. If the response received is a bad response, then if the good counter is less than or equal to the good counter threshold $N_G$, then the good counter is reset to zero and the good tracker is emptied.

If the response received is also not a bad response, then the system may determine that the response is an unreliable response and may ignore the response.

The signal processing routines may be applied to reduce the noise in the acquired EPs and to detect when EPs with inadequate signal to noise ratio (SNR) are acquired so that these EPs may be excluded from further analysis and the poor signal quality reported. The number of unreliable signals received may be tracked and compared with a threshold to determine when to create an alert regarding poor signal quality.

The filtering techniques applied may use likelihood-estimation based averaging to decrease instrumentation and context-based noise and increase the SNR of the acquired EPs such that baseline EPs can be more clearly defined and that changes in subsequent EPs can be better characterized and compared to the baseline and previous EPs.

Pattern recognition algorithms, for example, algorithms that match acquired waveforms to best fit curves, may be used. Such algorithms may be used to characterize the EPs, to measure changes in latter acquired EPs relative to the baseline and previous EPs and to detect when changes to the EPs, indicative of a changed functioning of the underlying sensory neural system, have occurred. EPs may be characterized using their energy, Euclidean distance and pseudo and cross correlations relative to a defined baseline template response as well as to previous EPs. Using these metrics, classification rules may be applied to determine if the current response indicates significant (adverse or recovering) changes to the underlying physiological system generating the EPs.

In an embodiment, a component may be added to allow medical or other attending personnel to reset the baseline response when the changes in the acquired EPs are not related to any underlying physiological change (e.g., changes related to stimulation or electrode factors). The apparatus may also obtain information from an anesthesia or blood pressure machine to calculate when changes in EP waveforms are due to anesthesia or blood pressure changes.

In various embodiments, as the EPDD 140 performs one or more of the functions described above, such as, for example, averaging evoked potentials, shifting baselines, and assessing changes in the waveforms, the EPDD 140 also sends data to an output device for display to the user. For example, in some embodiments, the computer 200 of the EPDD 140 includes a communications interface 224 that allows data to be transferred between the computer system 200 and an external user interface, such as a monitor, smartphone, or tablet. In some embodiments, the communications interface 224 is a USB port or other port configured to receive a cable connected to the external user interface. In other embodiments, the communications interface 224 is an interface for wireless communications, for example, a cellular, Wi-Fi, or RF antenna. The antenna of various embodiments is both a transmitter and receiver of signals.

Figure 20:
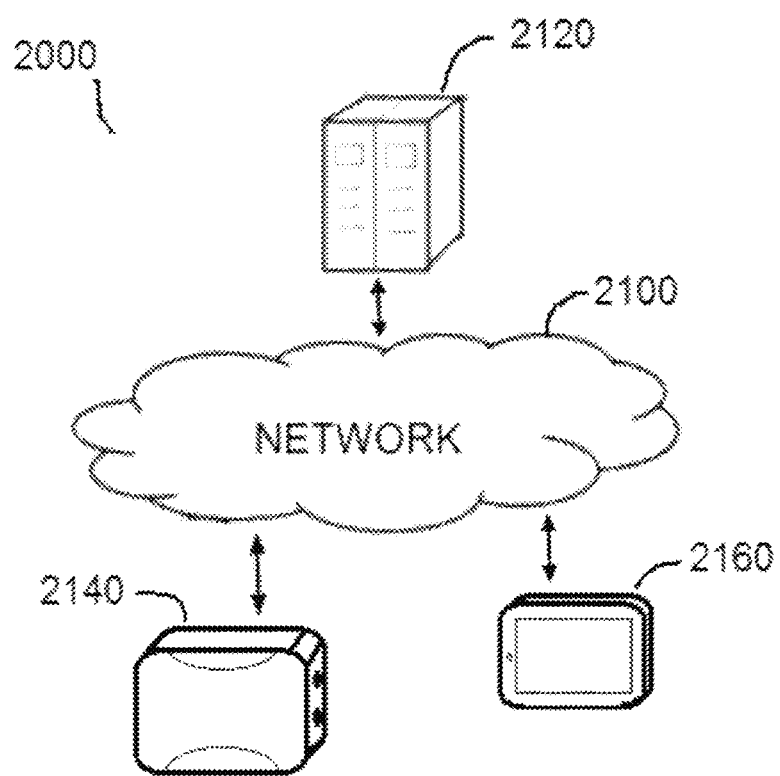
FIG. 20 depicts a schematic diagram of one embodiment of a system for detecting evoked potentials.

Another embodiment of a system for automatically detecting evoked potentials is provided in FIG. 20. Specifically, FIG. 20 illustrates a schematic diagram of at least some components found in one embodiment of a system for automatically detecting evoked potentials 2000 and the interactions between said components. One skilled in the art will appreciate that the embodiment is illustrative in nature only and various components and peripherals may be added, deleted, or substituted and various different hierarchies and modes of communication between the devices may be employed. In the depicted embodiment, the system 2000 is formed of a plurality of computerized devices, including an embodiment of the EPDD 2140, an embodiment of a display device 2160, and a back-end computer 2120. The EPDD 2140 of the depicted embodiment has some or all of the functionality and structure of other EPDD embodiments described elsewhere herein. Peripheral components such as, for example, cables and electrodes, are not shown, however, one skilled in the art will appreciate that in various embodiments, such components form part of the system 2000.

As depicted, the system 2000 includes one or more communication networks 2100 through which some or all of the various devices communicate with one another. In some embodiments, one or both of the EPDD 2140 and the display device 2160 transmit information to, and receive information from, the back-end computer 2120 via the communication network 2100. The network can be a local area network (LAN) or a wide area network (WAN). In some embodiments, the network is a wireless communication network, such as, for example, a mobile WiMAX network, LTE network, Wi-Fi network, or other wireless network. In other embodiments, communication between the EPDD 2140 and the back-end computer 2120, and/or communication between the display device 2160 and the back-end computer 2120, occurs over the internet via a wired network, such as, for example, a DSL cable connection, or over Ethernet or an intranet. In certain embodiments (not shown), the back-end computer 2120 is in wired connection with, or forms part of, the EPDD 2140; in such embodiments, no communication network is needed to transmit data and signals between the EPDD 2140 and the back-end computer 2120. In some embodiments, the EPDD 2140 and the display device 2160 transmit information to, and receive information from, each other via a communication network 2100. The network 2100 of such embodiments may include any of the networks mentioned above; additionally or alternatively, the network 2100 may represent a Bluetooth® connection, near-field communication connection, or other radio connection.

As depicted in FIG. 20, at least some of the devices of the system 2000 interact with the network 2100, and accordingly, each other, via a two-way (forward and reverse) communication link. The devices each include input/output devices for wired communication connections (e.g., modems, network cards, external data buses, ports, etc.) and/or wireless receivers and transmitters, which allow each device to transmit and receive information.

Figure 8:
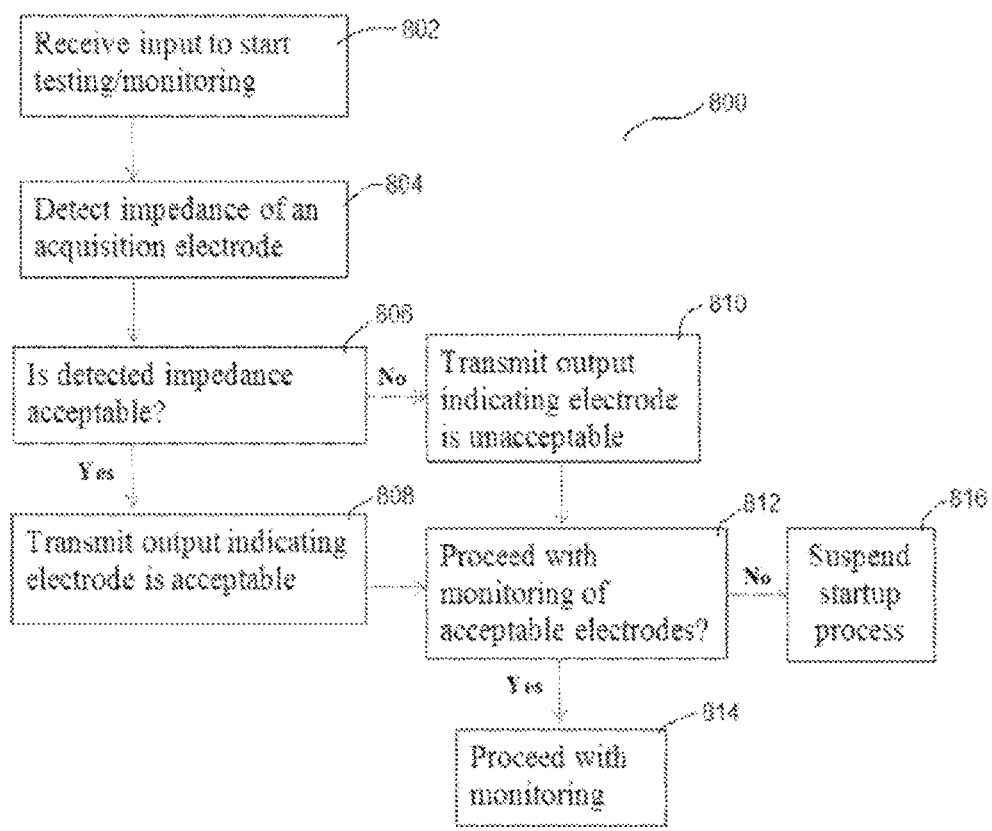
FIG. 8 depicts a flowchart of one embodiment of a method for automatically starting evoked potential monitoring.

In various embodiments, the EPDD 2140 includes a processor and memory, and software code is stored in the memory, which, when executed by the processor, causes the system to perform functions, such as, for example, any one or more of the following: perform a start-up/test protocol, such as, for example, the protocol depicted in FIG. 8; implement a stimulation protocol; receive raw EP signals from the recording electrodes; process the raw EP signals to remove noise, for example, by amplifying the signal and generating ensemble averaged EPs; identify and maintain supramaximal stimulation; suspend and resume data acquisition based on RF signals received from nearby equipment; transmit processed EP signals to a back-end computer 2120, etc.

In various embodiments, the back-end computer 2120 includes a processor and memory, and software code is stored in the memory, which, when executed by the processor, causes the system to perform back-end functions, such as, for example, any one or more of the following: receive EP readings from the EPDD 2140; store the EP readings in memory in a historical log; calculate a baseline from the EP readings; store the baseline in memory in a historical log; compare received EP readings to the current baseline; determine whether a change has occurred in a sequence of EPs, such as, for example, by performing a process such as any process described with reference to FIGS. 13A-19; identify when alerts are appropriate; transmit alerts and other information to the display device 2160 for display; receive requests for data from users via transmission of signals from the display device 2160; transmit the requested data to the display device 2160; etc.

In some embodiments, the back-end computer 2120 forms part of the EPDD 2140. For example, in some embodiments, the EPDD 2140 includes memory that stores code for both the EPDD 2140 functions and the back-end computer 2120 functions; in such embodiments, one processor may implement both sets of functions. In certain other embodiments, the back-end computer is a personal computer or other machine in wired or wireless communication with the EPDD 2140. In some embodiments, the back-end computer 2120 is a server. In some such embodiments, the back-end computer 2120 includes an application server, a webserver, and/or a database server. It will be appreciated to one skilled in the art that the back-end computer 2120 may be formed of any suitable number of servers. For example, in some embodiments, the back-end computer 2120 includes one or a plurality of application servers, one or a plurality of webservers, and/or one or a plurality of database servers.

In various embodiments, the display device 2160 includes a processor, memory with application software stored in the memory, and one or more input/output devices (e.g., mouse, keyboard, touchscreen, monitor, etc.) that allow it to receive inputs from a user and display graphical outputs to the user. In various embodiments, the application software, when executed by the processor, causes the display device 2160 to perform front-end functions such as, for example: displaying a graphical user interface (GUI); receiving data from the back-end computer 2120; displaying data received from the back-end computer 2120 within the GUI, receiving user inputs and user requests for data via the GUI; transmitting the user requests for data to the back-end computer 2120; etc.

Figure 21:
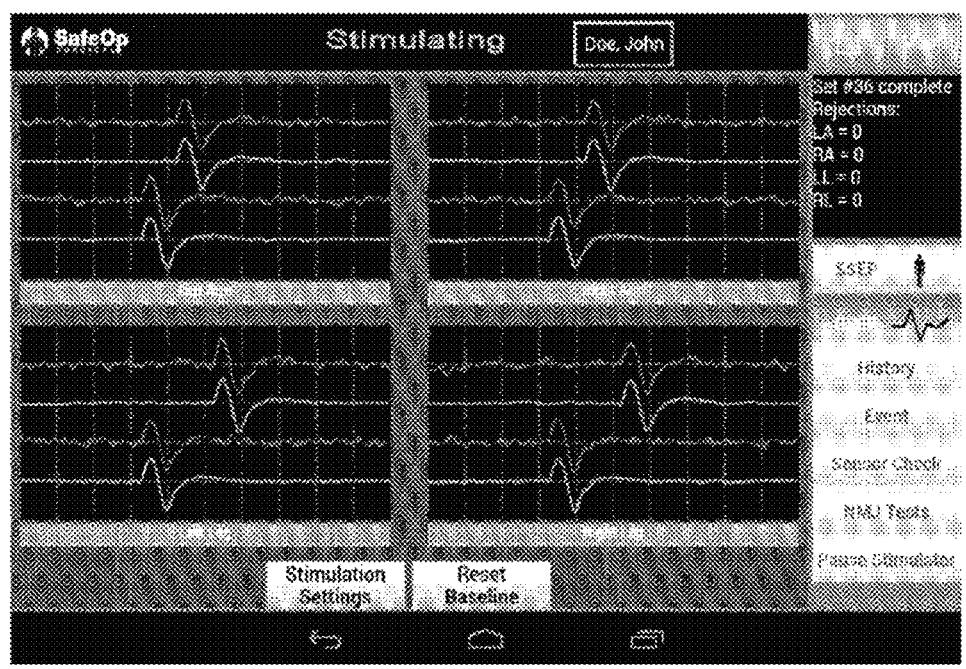
FIGS. 21-24 each depict one embodiment of a user interface in accordance with embodiments disclosed herein.
Figure 22:
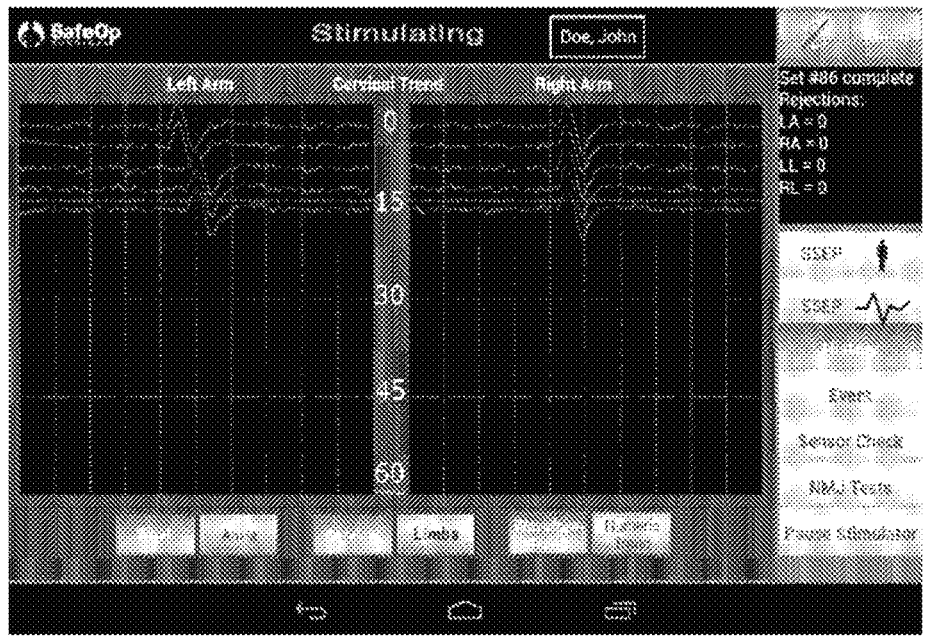
Figure 23:
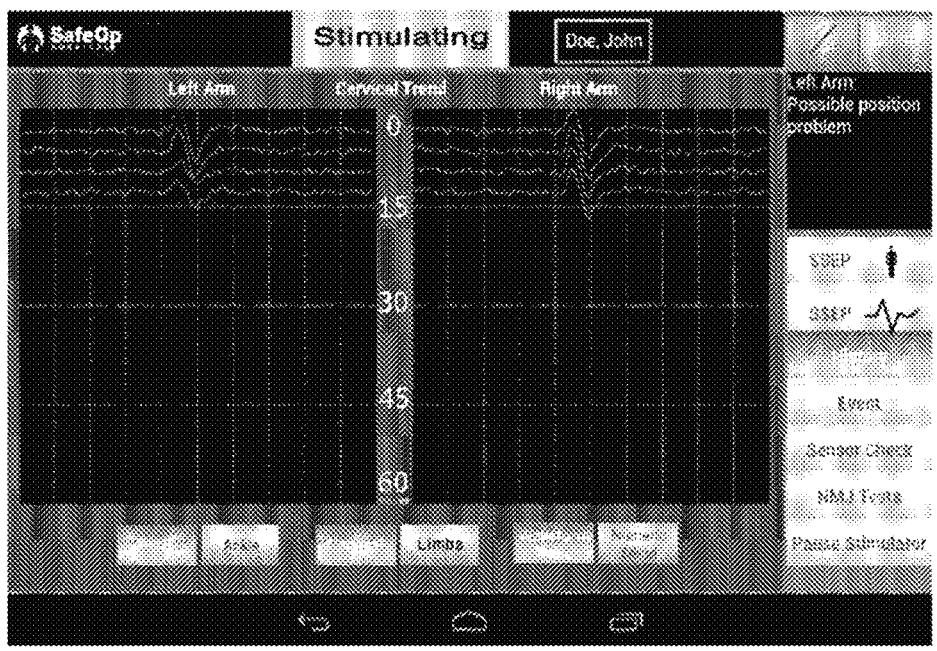
Figure 24:
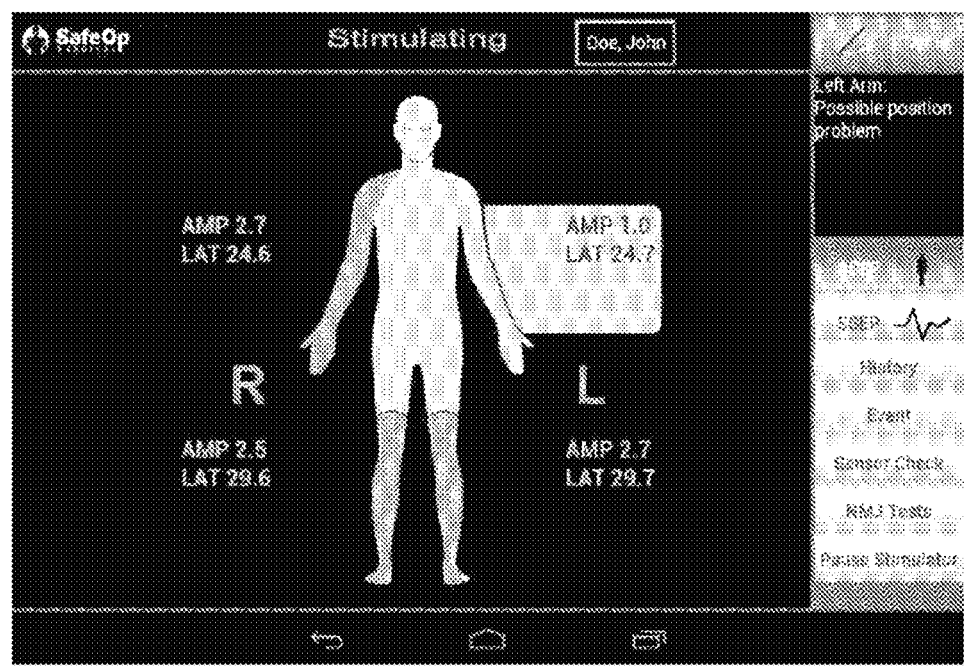

In some embodiments, the GUI presents data in easy-to-read and easy-to-interpret formats. In some embodiments, the GUI provides users with the option of viewing recorded data in traditional or easy-to-read/non-traditional formats. For example, in some embodiments, the waveforms produced from the recorded signals can be presented via the GUI. One example of the presentation of such data is provided in FIG. 21. Additionally or alternatively, in various embodiments, a history of the recorded waveforms can be viewed. In some embodiments, the provided history spans a particular duration of time, for example, 10 minutes, 15 minutes, 30 minutes, 60 minutes, 2 hours, the duration of a surgical procedure, etc. Examples of the presentation of historical recordings are provided in FIGS. 22 and 23. Trends may become visible by looking at the historical recordings. For example, an increase in signal latency is visible in the waveform of FIG. 22 and a decrease in amplitude is visible in the waveform of FIG. 23. In some embodiments, the GUI presents a summary of the acquired data in real time in a pictorial format. For example, as shown in FIG. 24, in some embodiments, the GUI utilizes colors and/or pictures to indicate whether signals received from a particular limb or body portion are Good, Bad, Undetermined/borderline, or Unreliable. With some such embodiments, a user such as an anesthesiologist or nurse is able to identify impending peripheral nerve injuries with a quick glance at the user interface.

In some embodiments, the system 2000 further includes one or more additional components, such as, for example, a smart bed or a robotic surgical unit. As one non-limiting example, in some embodiments, the system 2000 includes a smart table having a table integration unit. Examples of tables and table integration units are described in U.S. application Ser. No. 12/620,384, the disclosure of which is herein incorporated by reference in its entirety. The table may include, e.g., but is not limited to, any surface upon which a patient may be placed, such as a bed, a chair, an operating room table, a pre-op table, and/or a post-op table, etc. In certain embodiments, the table integration unit is mechanically and/or electronically coupled to, or incorporated into, the table and/or the EPDD, enabling the EPDD to send signals that control movement of the bed. For example, in certain exemplary embodiments, the EPDD may detect a potential nerve injury such as a positioning effect in a patient lying on the table using stimulating electrodes and recording electrodes, and the EPDD may correct the detected potential nerve injury by instructing the table integration unit to raise, lower, or otherwise adjust the position of the table or a portion thereof to adjust the position of the patient.

As another non-limiting example, the system 2000 of some embodiments includes a robotic surgery system, such as, for example, the robotic surgery system described in U.S. Appl. Publication No. 2013/0211419 A1 (U.S. application Ser. No. 13/728,756) or U.S. Pat. No. 8,400,094, the disclosures of which are both herein incorporated by reference in their entireties. For example, one or more of the methods and/or systems and devices described herein can be utilized with, combined with, and/or integrated with the systems and/or methods of the incorporated robotic surgery systems and methods. In some instances, the methods of this application can be utilized with any of the methods described in those publications. In some instances, the systems and devices of this application can be utilized and combined with any of the methods described in those publication. The EPDD 2140 of some embodiments is in wired or wireless communication with the robotic surgery system, such that, when the EPDD detects a potential nerve injury such as a positioning effect in a patient, the EPDD 2140 can transmit signals to the robotic surgery system instructing the robotic surgery system to adjust the position of the patient, for example, by adjusting the position of the patient table. In other embodiments, the EPDD 2140 is simply used in tandem with the robotic surgery system, advantageously enabling detection and timely correction of potential nerve injuries, such as positioning effect, during surgery. The EPDD 2140 may be used in tandem with any robotic surgery system, such as, for example, but not limited to robotic surgery systems manufactured by Intuitive Surgical Operations, Inc., Hansen Medical Inc., MAKO Surgical Corp., Mazor Robotics Ltd., and Titan Medical Inc., which systems are incorporated herein by reference in in their entireties. In some embodiments, the EPDD 2140 permanently or non-permanently couples to a portion of a robotic surgery system, such as, for example, to a patient table or a mobile base. The EPDD 2140 may be used to monitor potential nerve injuries in any surgery, including in any surgery performed partially or entirely robotically.

In some embodiments, a method of performing surgery includes performing a robotically-assisted surgical procedure, such as, for example, a robotically-assisted hysterectomy, other gynecologic surgical procedure, prostatectomy, urologic surgical procedure, general laparoscopic surgical procedure, thoracoscopic surgical procedure, valve replacement, other cardiac surgical procedure, bariatric surgery, other gastrointestinal surgical procedure, or oncological surgical procedures, among others. The method of some embodiments further includes delivering an electrical stimulus to a peripheral nerve in the body, recording a resultant electrical waveform generated by the body's nervous system in response to the electrical stimulus, and monitoring the resultant electrical waveform to detect changes indicative of potential nerve injury. Additionally or alternatively, in some embodiments, the method of performing surgery may include any of the methods for detecting the functionality of one or more nerves described elsewhere herein. The methods of detecting functionality of one or more nerves or of using the EPDD 2140 may be incorporated at any juncture of a robotic surgery. For example, such methods can be performed at multiple times, continuously, at pre-selected situations such as when certain types of procedures are initiated or concluded (including any of those mentioned above), and so forth. The method of various embodiments further includes adjusting the position of a patient when a potential nerve injury or abnormality is detected.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

Although the foregoing has included detailed descriptions of some embodiments by way of illustration and example, it will be readily apparent to those of ordinary skill in the art in light of the teachings of these embodiments that numerous changes and modifications may be made without departing from the spirit or scope of the appended claims.

What is claimed is:

1. A method for intraoperative determination and monitoring of a plurality of resultant electrical waveforms of a patient, the method comprising:
   stimulating, via a stimulating electrode positioned on skin of the patient, the stimulating comprising transmitting a plurality of time-locked electrical stimuli, the stimulating electrode in communication with an evoked potential detection device configured to monitor one or more peripheral nerves of the patient;
   recording, via a recording electrode positioned on the skin of the patient, the plurality of resultant electrical waveforms received by the evoked potential detection device, the resultant electrical waveforms generated by the body's nervous system in response to the time-locked electrical stimuli;
   developing, by the evoked potential detection device, an initial baseline waveform from an average of the plurality of resultant electrical waveforms;
   stimulating, via the stimulating electrode by the evoked potential detection device, an additional electrical stimulus;
   recording, via the recording electrode by the evoked potential detection device, an additional resultant electrical waveform;
   determining, by the evoked potential detection device, if the additional resultant electrical waveform should be indicated as a good response by:
      comparing, by the evoked potential detection device, the additional resultant electrical waveform to the initial baseline waveform;
      if the additional resultant electrical waveform should be indicated as a good response, developing, by the evoked potential detection device, an updated baseline waveform, wherein the updated baseline waveform is a weighted average of the initial baseline waveform and the additional resultant electrical waveform; and
      if the additional resultant electrical waveform should not be indicated as a good response, setting the updated baseline waveform to the initial baseline waveform.

2. The method of claim 1, further comprising sending, by the evoked potential detection device, a data output to a user interface, the data output comprising an indication of whether the additional resultant electrical waveform is acceptable.

* * * * *